(12) United States Patent
Mchatton et al.

(10) Patent No.: US 10,577,738 B2
(45) Date of Patent: Mar. 3, 2020

(54) MITIGATION OF ODOR IN CLEANING MACHINES AND CLEANING PROCESSES

(71) Applicants: NOVOZYMES BIOLOGICALS, INC., Salem, VA (US); HENKEL AG & CO. KGAA, Dusseldorf (DE)

(72) Inventors: Sarah C. Mchatton, Wake Forest, NC (US); I. Michelle Williams, Durham, NC (US); Alejandro Penaloza-Vazquez, Roanoke, VA (US); Jonathan Leder, Montvale, VA (US)

(73) Assignees: NOVOZYMES BIOLOGICALS, INC., Salem, VA (US); Henkel AG & CO. KGAA, Dusseldorf (DE)

(*) Notice: Subject to any disclaimer, the term of this patent is extended or adjusted under 35 U.S.C. 154(b) by 0 days.

(21) Appl. No.: 15/962,676

(22) Filed: Apr. 25, 2018

(65) Prior Publication Data

US 2018/0245259 A1 Aug. 30, 2018

Related U.S. Application Data

(62) Division of application No. 15/195,597, filed on Jun. 28, 2016, now Pat. No. 9,982,382, which is a division of application No. 14/596,717, filed on Jan. 14, 2015, now Pat. No. 9,404,208, which is a division of application No. 13/397,570, filed on Feb. 15, 2012, now Pat. No. 9,228,284.

(60) Provisional application No. 61/443,055, filed on Feb. 15, 2011.

(51) Int. Cl.
| | |
|---|---|
| C12N 1/20 | (2006.01) |
| A61L 9/01 | (2006.01) |
| D06F 35/00 | (2006.01) |
| C11D 3/38 | (2006.01) |
| C11D 11/00 | (2006.01) |
| A61L 9/013 | (2006.01) |
| C12R 1/07 | (2006.01) |
| C12R 1/00 | (2006.01) |

(52) U.S. Cl.
CPC ............ *D06F 35/008* (2013.01); *A61L 9/01* (2013.01); *A61L 9/013* (2013.01); *C11D 3/381* (2013.01); *C11D 11/0017* (2013.01); *C12N 1/20* (2013.01); *C12R 1/00* (2013.01); *C12R 1/07* (2013.01); *A61L 2202/14* (2013.01)

(58) Field of Classification Search
None
See application file for complete search history.

(56) References Cited

U.S. PATENT DOCUMENTS

| | | |
|---|---|---|
| 5,811,287 A | 9/1998 | Aoshima |
| 5,821,112 A | 10/1998 | Botto |
| 6,080,391 A | 6/2000 | Tsuchiya |
| 6,197,040 B1 | 3/2001 | Horner |
| 6,197,070 B1 | 3/2001 | Horner |
| 6,197,740 B1 | 3/2001 | Shikata |
| 6,376,451 B1 | 4/2002 | Teasdale |
| 6,610,642 B2 | 8/2003 | Ghosh |
| 6,927,055 B2 | 8/2005 | Poulose |
| 8,409,591 B2 | 4/2013 | Farmer |
| 9,404,208 B2 | 8/2016 | McHatton |
| 9,982,382 B2 * | 5/2018 | McHatton ............... A61L 9/013 |
| 2002/0128167 A1 | 9/2002 | Ghosh |
| 2003/0089381 A1 | 5/2003 | Manning, Jr. |
| 2009/0318292 A1 | 12/2009 | Kang |
| 2009/0324533 A1 | 12/2009 | Snyder |
| 2011/0274676 A1 | 11/2011 | Farmer |
| 2012/0207699 A1 | 8/2012 | McHatton |

FOREIGN PATENT DOCUMENTS

| | | |
|---|---|---|
| CN | 101575807 A | 7/2011 |
| CN | 102115697 B | 7/2011 |
| JP | 10249388 A | 9/1998 |
| JP | 2001-299328 A | 10/2001 |
| JP | 2002-161481 A | 6/2002 |
| JP | 2002-226893 | 8/2002 |
| JP | 2003-253299 | 9/2003 |
| JP | 2006-104257 | 4/2006 |
| WO | 96/34108 A2 | 10/1996 |
| WO | 99/20726 A1 | 4/1999 |
| WO | 00/01354 A1 | 1/2000 |
| WO | 00/03752 A1 | 1/2000 |
| WO | 00/34450 A1 | 6/2000 |
| WO | 00/61201 A2 | 10/2000 |
| WO | 01/13927 A2 | 3/2001 |
| WO | 02/33035 A1 | 4/2002 |
| WO | 02/066591 A1 | 8/2002 |
| WO | 03/064755 A2 | 8/2003 |
| WO | 03/099987 A1 | 12/2003 |
| WO | 03/104376 A1 | 12/2003 |
| WO | 2008/021761 A2 | 2/2008 |
| WO | 2008/118749 A2 | 10/2008 |
| WO | 2009/148800 A1 | 12/2009 |
| WO | 2010/006235 A1 | 1/2010 |
| WO | 2010/014715 A1 | 2/2010 |
| WO | 2011/163500 A2 | 12/2011 |

OTHER PUBLICATIONS

Gao et al., Journal of Applied Polymer Science, vol. 117, No. 5, pp. 3075-3082 (2010).
Gupta et al., Appl. Microbiol. Biotechnol., vol. 59, pp. 15-32 (2002).
Munk et al., Journal of Surfactants and Detergents, vol. 3, No. 4, pp. 505-515 (2000).
Munk et al., Journal of Surfactants and Detergents, vol. 4, No. 4, pp. 385-394 (2001).
Nagoh et al., Tenside Surf. Det., vol. 42, No. 1, pp. 7-12 (2005).
Novozymes, Carpet Ease Spot product sheet (2010).
Novozymes, Freshen Free product sheet (2011).

(Continued)

*Primary Examiner* — Padmavathi Baskar
(74) *Attorney, Agent, or Firm* — Elias Lambiris

(57) ABSTRACT

The invention relates to malodor controlling bacteria and related methods and compositions for the control and prevention of malodor.

14 Claims, No Drawings

(56) References Cited

OTHER PUBLICATIONS

Obendorf, AATCC Review, vol. 4, No. 1, pp. 17-23 (2004).
Ruiz-Garcia et al., International Journal of Systematic and Evolutionary Microbiology, vol. 55, No. 1, pp. 191-195 (2005).
Yue et al., China Surfactant Soap and Detergent Industries, vol. 3, pp. 30-39 (2009).

* cited by examiner

MITIGATION OF ODOR IN CLEANING MACHINES AND CLEANING PROCESSES

CROSS-REFERENCE TO RELATED APPLICATIONS

This application is a divisional of U.S. application Ser. No. 15/195,597 filed Jun. 28, 2016, now U.S. Pat. No. 9,982,382, which is a divisional of U.S. patent application Ser. No. 14/596,717 filed on Jan. 14, 2015, now U.S. Pat. No. 9,404,208, which is a divisional of U.S. patent application Ser. No. 13/397,570 filed Feb. 15, 2012, now U.S. Pat. No. 9,228,284, which claims priority or the benefit under 35 U.S.C. 119 of U.S. provisional application No. 61/443,055 filed Feb. 15, 2011. The content of these applications is fully incorporated herein by reference.

FIELD OF THE INVENTION

The present invention relates generally to malodor inhibition in cleaning machines, cleaning processes, and/or articles treated in the cleaning machine/process.

BACKGROUND

Malodor is a growing problem, particularly in laundry, with the changed habits of lower temperature washing, front load wash machines that save water but leave behind residual water between loads allowing bacterial biofilms to flourish, line drying clothes to save energy rather than appliance drying, and the increased popularity of manmade fabrics, such as athletic wear, that appear to retain odors more than natural fabrics.

Major detergent manufacturers attempt to solve the problem with perfumes. These solutions, however, are not completely effective as they are short-term. There is a need in the art for new solutions for controlling the problem of malodor.

SUMMARY

The present invention provides methods and composition for inhibiting malodor in a cleaning machine, cleaning process or article treated (cleaned) in a cleaning machine or cleaning process, comprising contacting a cleaning machine, cleaning process and/or article treated in the cleaning machine/process with at least one microorganism which is able to inhibit malodor caused by a malodor causing microorganism (e.g., bacteria) present in the cleaning machine, cleaning process or article treated in the cleaning machine or cleaning process. The malodor source may be at least one malodor causing microorganism (e.g., bacteria) and/or the at least one microorganism (e.g., bacteria) capable of causing malodor.

The methods and compositions of the present invention may be used to treat an existing odor problem and/or as a preventative treatment to prevent a potential odor problem. The present invention may be used, for example, to inhibit malodor in laundry washing machines/processes, dry cleaning machines/processes, steam cleaning machines/processes, carpet cleaning machines/processes, dish washing machines/processes, and other cleaning machines/processes. In a particular aspect, the present invention provides methods for controlling odor in laundry by contacting a laundry machine, laundry washing process, laundry and/or laundered fabric with at least one microorganism which is able to inhibit production of malodor in laundry. The contacting can occur before, during, or after the laundry washing process.

The present invention also provides compositions for use in inhibiting malodor in cleaning machines and cleaning processes. Compositions of the present invention comprise and at least one microorganism capable of inhibiting malodor as an ingredient of a solid, semi-solid, gel, liquid, aerosol, emulsion, or powder composition. In one aspect, the composition is adapted for application to the interior of a cleaning machine (washing machines, dry cleaning machines, steam cleaning machines, carpet cleaning machines, dish washing machines, and other cleaning machines), and comprises a carrier and at least one microorganism capable of inhibiting malodor in the cleaning machine. In another aspect, the composition is adapted for application directly to an article cleaned in the cleaning machine or cleaning process, such as, to a fabric (clean or uncleaned laundry) or other article cleaned in the cleaning machine or cleaning process. In a particular embodiment, the compositions of the presentation may be included as a component of a detergent, a fabric softener, or other cleaning composition.

The present invention also provides an apparatus containing the compositions of the present invention for use in controlling malodor. The apparatus may be adapted for administering an effective dosage of at least one microorganism which is able to inhibit malodor to the interior of a washing machine or fabric for a defined period of use.

DETAILED DESCRIPTION OF THE INVENTION

As used herein, "inhibiting" or "inhibit" malodor means preventing, reducing and/or substantially eliminating malodor caused by odor-causing microorganism (e.g., bacteria). Preventing, reducing, and/or substantially eliminating the odor may occur by one or more effects associated with the at least one microorganism (e.g., bacterial strain) of the invention. These effects include, but are not limited to, inhibition of growth of the odor-causing microorganims (e.g., bacterial species causing malodour), inhibition of the production or secretion of odorous volatile substances by odor-causing microorganism (e.g., bacteria), inhibition of the conversion of a chemical precursor into an odorous substance, consumption by the at least one microorganims of the odor volatiles as a food source, consumption by the at least one microorganism of the chemical precursor of the odorous substance as a food source, and/or by modification of the odorous substance, each upon contact with the at least one microorganism or a substance derived therefrom. Particular embodiments are directed at inhibiting maldor caused by odor-causing bacteria in a laundry machine, laundry process and/or laundered fabrics by treating a laundry machine, laundry process and/or laundered fabrics with at least one bacteria which is able to inhibit the malodor.

Malodor may be generated from a number of bacterial sources (including compounds derived or produced therefom). Sources of malodor causing bacteria, include bacterium species selected from the group consisting of *Bacillus amyloliquefaciens, Acinetobacter junii, Bacillus subtilis, Janibacter melois, Sphingobium ummariense, Sphingomonas panni,* Sphingomonadaceae, *Actinobacter tandoii, Junibacter melonis, Curtobacterium flaccumfaciens* subsp. *flaccumfaciens, Flavobacterium denitrificans, Staphylococcus epidermidis, Escherichia coli, Leclercia adecarboxylata, Enterobacter* sp., *Cronobacter sakazakii, Bacillus megate-*

*rium, Sphingobacterium faecium, Enterobacter cloacae, Pseudomonas veronii, Microbacterium luteolum, Morganella morganii, Bacillus cereus, Pseudomonas* sp., *Pseudomonas-marginalis, Citrobacter* sp., *Escherichia coli* strain JCLys5, *Roseomonas aquatic, Pseudomonas panipatensis, Brevibacillus subtilis subtilis, Micrococcus luteus, Bacillus pumilus, Ralstonia eutropha, Caulobacter fusiformis, Stenotrophomonas maltophilia, Rhodococcus opacus, Breviundimonas intermedia, Agrobacterium tumefaciens,* and/or a combination thereof, and/or substances derived therefrom.

Any microorganism that is able to inhibit malodor may be used in the present invention. In particular embodiments, the microorganism is a bacteria. Combinations of one or more of such microorganisms may also be used, such as, blends of two or more strains, three or more strains, four or more strains, five or more strains, etc. A microorganism that is able to inhibit malodor is a species (or strain) of a microorganism that has action against the odor-causing organism or against the odor-causing compound (e.g., volatile substance) produced or derived from the odor-causing organism so as to reduce or eliminate the perceived odor arising from such odor-causing organisms or odor-causing compound. The action to reduce or eliminate the perceived odor may include degradation of the odor-causing compound after secretion by the odor-causing organism or prevention of the production of such odor-causing compound. In other embodiments, the present invention is directed to a substance derived from a microorganism which has action against the odor-causing organism or against the odor-causing compound (e.g., volatile substance) produced or derived from the odor-causing organism so as to reduce or eliminate the perceived odor arising from such odor-causing organisms or odor-causing compound. In still another embodiment, the present invention is directed to decreasing malodor, measurable at least by the results of a human odor panel and/or Gas Chromatography-Mass Spectrometer (GC-MS) analysis of known odor-causing compound(s) (e.g., volatile substances), comprising treating articles, articles subjected to a cleaning machine or cleaning process, and/or cleaning machines with at least one microorganism, or substance derived therefrom, that either directly or indirectly inhibits malodor, compared to untreated articles, untreated articles subjected to a cleaning machine or cleaning process, and/or untreated cleaning machines.

In one embodiment, the at least one microorganism is a species of *Bacillus*, for example, at least one species of *Bacillus* selected from the group consisting of *Bacillus subtilis, Bacillus amyloliquefaciens, Bacillus licheniformis, Bacillus amyloliquefaciens, Bacillus pumilus* or a combination thereof. In yet another embodiment, the at least one microorganism is a species of *Bacillus* selected from the group consisting of *Bacillus pumilus* strain NRRL B-50016; *Bacillus amyloliquefaciens* strain NRRL B-50017, *Bacillus amyloliquefaciens* strain PTA-7792; *Bacillus amyloliquefaciens* strain PTA-7543; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus subtilis* strain PTA-7547; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; and *Bacillus licheniformis* strain NRRL B-50015, or a combination thereof. The at least one strain of *Bacillus* may in a particular embodiment be selected from the group consisting of *Bacillus pumilus* strain NRRL B-50016; *Bacillus amyloliquefaciens* strain PTA-7543; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7791; *Bacillus subtilis* strain NRRL B-50136; *Bacillus amyloliquefaciens* strain NRRL B-50141; and *Bacillus amyloliquefaciens* strain NRRL B-50399 or a combination thereof. In a particular embodiment, the at least one strain of *Bacillus* is selected from the group consisting of *Bacillus amyloliquefaciens* strain PTA-7541; *Bacillus amyloliquefaciens* strain PTA-7543 *Bacillus amyloliquefaciens* strain PTA-7546; *Bacillus amyloliquefaciens* strain PTA-7549; *Bacillus amyloliquefaciens* strain NRRL B-50141; *Bacillus amyloliquefaciens* strain NRRL B-50706; and *Bacillus subtilis* strain NRRL B-50136 or a combination thereof.

In another embodiment, the at least one microorganism is a microorganism that is capable of using the at least one odiferous compound(s) as a food source. Such microorganism may be selected from the group consisting of *Bacillus pumilus* strain NRRL B-50016; *Bacillus amyloliquefaciens* strain NRRL B-50017, *Bacillus amyloliquefaciens* strain PTA-7792; *Bacillus amyloliquefaciens* strain PTA-7543; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus subtilis* strain PTA-7547; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; and *Bacillus licheniformis* strain NRRL B-50015, or a combination thereof. In another embodiment, the at least one microorganism capable of using the at least one odiferous compound(s) as a food source is selected from the group consisting of *Bacillus pumilus* strain NRRL B-50016; *Bacillus amyloliquefaciens* strain PTA-7543; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7791; *Bacillus subtilis* strain NRRL B-50136; *Bacillus amyloliquefaciens* strain NRRL B-50141; and *Bacillus amyloliquefaciens* strain NRRL B-50399 or a combination thereof. In yet another embodiment, the at least one microorganism capable of using the at least one odiferous compound(s) as a food source is selected from the group consisting of *Bacillus amyloliquefaciens* strain PTA-7541; *Bacillus amyloliquefaciens* strain PTA-7543 *Bacillus amyloliquefaciens* strain PTA-7546; *Bacillus amyloliquefaciens* strain PTA-7549; *Bacillus amyloliquefaciens* strain NRRL B-50141; *Bacillus amyloliquefaciens* strain NRRL B-50706; and *Bacillus subtilis* strain NRRL B-50136 or a combination thereof.

In another aspect, the at least one microorganism includes strains that are closely related to any of the above strains on the basis of 16S rDNA sequence identity. See Stackebrandt E, et al., "Report of the ad hoc committee for the re-evaluation of the species definition in bacteriology," *Int J Syst Evol Microbiol.* 52(3):1043-7 (2002) regarding use of 16S rDNA sequence identity for determining relatedness in bacteria. In an embodiment, the at least one strain is at least 95% identical to any of the above strains on the basis of 16S rDNA sequence identity, at least 96% identical to any of the above strains on the basis of 16S rDNA sequence identity, at least 97% identical to any of the above strains on the basis of 16S rDNA sequence identity, at least 98% to any of the above strains on the basis of 16S rDNA sequence identity, at least 98.5% identical to any of the above strains on the basis of 16S rDNA sequence identity, at least 99% identical to any of the above strains on the basis of 16S rDNA sequence identity or at least 99.5% to any of the above strains on the basis of 16S rDNA sequence identity.

Microorganisms which generate zones of inhibition (ZOIs) against key malodor causing microorganisms of at least 3 mm, at least 4 mm, at least 5 mm, or at least 6 mm and above may be possible biocontrol agents and, therefore, candidate microorganisms for reducing malodor in accordance with the present invention. Accordingly, the present invention includes a method of screening for prospective malodor inhibiting microorganisms by testing for the inhibition of species (e.g., using ZOI assays as described in Example 3 below) selected from the genera consisting of *Bacillus* spp., *Acinetobacter* spp., *Janibacter* spp., *Sphingobium* spp., *Sphingomonas* spp., *Actinobacter* spp., *Junibacter* spp., *Curtobacterium* spp., *Flavobacterium* spp., *Staphylococcus* spp., *Escherichia* spp., *Leclercia* spp., *Enterobacter* sp., *Cronobacter* spp., *Sphingobacterium* spp., *Pseudomonas* spp., *Microbacterium* spp., *Morganella* spp., *Citrobacter* spp., *Roseomonas* spp., *Brevibacillus* spp., *Micrococcus* spp., *Ralstonia* spp., *Caulobacter* spp., *Stenotrophomonas* spp., *Rhodococcus* spp., *Breviundimonas* spp., *Agrobacterium* spp., or combinations thereof. The present invention further includes screening for prospective malodor inhibiting microorganism by testing for the inhibition of species (e.g., using ZOI assays as described in Example 3 below) selected from the group consisting of *Bacillus amyloliquefaciens, Acinetobacter junii, Bacillus subtilis, Janibacter melois, Sphingobium ummariense, Sphingomonas panni,* Sphingomonadaceae, *Actinobacter tandoii, Junibacter melonis, Curtobacterium flaccumfaciens* subsp. *flaccumfaciens, Flavobacterium denitrificans, Staphylococcus epidermidis, Escherichia coli, Leclercia adecarboxylata, Enterobacter* sp., *Cronobacter sakazakii, Bacillus megaterium, Sphingobacterium faecium, Enterobacter cloacae, Pseudomonas veronii, Microbacterium luteolum, Morganella morganii, Bacillus cereus, Pseudomonas* sp., *Pseudomonas-marginalis, Citrobacter* sp., *Escherichia coli* strain JCLys5, *Roseomonas aquatic, Pseudomonas panipatensis, Brevibacillus subtilis subtilis, Micrococcus luteus, Bacillus pumilus, Ralstonia eutropha, Caulobacter fusiformis, Stenotrophomonas maltophilia, Rhodococcus opacus, Breviundimonas intermedia, Agrobacterium tumefaciens,* and/or a combination thereof, and/or substances derived therefrom. Also, the effect of these strains on production of the volatiles, prevention or reduction in conversion of precursor to such volatiles, or consumption of the volatiles can indicate usefulness in the compositions and methods of the invention. Further still, analyses of sole carbon source utilization study are effective in determining whether microorganisms generally, and NZB strains NRRL B-50136, NRRL B-50014, NRRL B-50015, NRRL B-50016, NRRL B-50017, NRRL B-50141, NRRL B-50018, PTA-7541, PTA-7792, PTA-7543, PTA-7544, PTA-7545, PTA-7546, PTA-7547, PTA-7549, PTA-7793, PTA-7790, PTA-7791, NRRL B-50706, and NRRL B-50399 more specifically, have the capability to grow on and/or biodegrade odorous compounds associated with malodor in laundry. Further still, odor studies were effective in determining whether microorganisms generally, and NZB strains NRRL B-50136, NRRL B-50014, NRRL B-50015, NRRL B-50016, NRRL B-50017, NRRL B-50141, NRRL B-50018. PTA-7541, PTA-7792, PTA-7543, PTA-7544, PTA-7545, PTA-7546, PTA-7547, PTA-7549, PTA-7793, PTA-7790, PTA-7791, NRRL B-50706, and NRRL B-50399 more specifically, inhibit and/or prevent laundry malodor.

The following biological material has been deposited under the terms of the Budapest Treaty at American Type Culture Collection (ATCC), 10801 University Blvd., Manassas, Va. 20108, USA, and the Microbial Genomics and Bioprocessing Research Unit (NRRL) National Center for Agricultural Utilization Research 1815 N. University Street, Peoria, Ill. 61604, USA and given the following accession number:

| Identification | Accession Number | Date of Deposit |
| --- | --- | --- |
| *Bacillus licheniformis* | NRRL B-50014* | Mar. 14, 2007 |
| *Bacillus licheniformis* | NRRL B-50015 | Mar. 14, 2007 |
| *Bacillus pumilus* | NRRL B-50016 | Mar. 14, 2007 |
| *Bacillus amyloliquifaciens* | NRRL B-50017 | Mar. 14, 2007 |
| *Bacillus amyloliquifaciens* | NRRL B-50141 | Jun. 3, 2008 |
| *Bacillus amyloliquifaciens* | NRRL B-50018 | Mar. 14, 2007 |
| *Bacillus amyloliquifaciens* | PTA-7541** | Apr. 20, 2006 |
| *Bacillus amyloliquifaciens* | PTA-7792 | Aug. 18, 2006 |
| *Bacillus amyloliquifaciens* | PTA-7543 | Apr. 20, 2006 |
| *Bacillus amyloliquifaciens* | PTA-7544 | Apr. 20, 2006 |
| *Bacillus amyloliquifaciens* | PTA-7545 | Apr. 20, 2006 |
| *Bacillus amyloliquifaciens* | PTA-7546 | Apr. 20, 2006 |
| *Bacillus subtilis* subsp.*subtilis* | PTA-7547 | Apr. 20, 2006 |
| *Bacillus amyloliquifaciens* | PTA-7549 | Apr. 20, 2006 |
| *Bacillus amyloliquifaciens* | PTA-7793 | Aug. 18, 2006 |
| *Bacillus amyloliquifaciens* | PTA-7790 | Aug. 18, 2006 |
| *Bacillus amyloliquifaciens* | PTA-7791 | Aug. 18, 2006 |
| *Bacillus amyloliquifaciens* | NRRL B-50399 | Jun. 16, 2010 |
| *Bacillus subtilis* subsp. *subtilis* | NRRL B-50136 | May 30, 2010 |
| *Bacillus amyloliquifaciens* | NRRL B-50706 | Feb. 2, 2012 |

*NRRL indicates deposit with the Agricultural Research Service Culture Collection, Peoria, IL
**PTA indicates deposit with the American Type Culture Collection The strain(s) has/have been deposited under conditions that assure that access to the culture will be available during the pendency of this patent application to one determined by the Commissioner of Patents and Trademarks to be entitled thereto under 37 C.F.R. § 1.14 and 35 U.S.C. § 122. The deposit represents a pure culture of the deposited strain. The deposit is available as required by foreign patent laws in countries wherein counterparts of the subject application or its progeny are filed. However, it should be understood that the availability of a deposit does not constitute a license to practice the subject invention in derogation of patent rights granted by governmental action.

The methods and compositions of the present invention may be applied to cleaning machines, cleaning processes, and articles treated (e.g., cleaned) in the clearning machines and processes. Cleaning machines and cleaning processes which may be treated include, without limitiation, a laundry cleaning machine/process (e.g., in wash cycle), a dry cleaning machine/process, a steam cleaning machine/process, a carpet cleaning machine/process, or a dish washing machine/process. The method and compositions of the present invention may be applied to a new machine or a machine following the use of such machine. The method and compositions of the present invention may be applied to one or more process steps in the clearning processes (such as, in the wash cycle of laundering washing or dish washing machine).

The methods and compositions may also be applied directly to an article treated (e.g., cleaned) in the cleaning machine or cleaning process, such as, to a laundry treated in the machine. The article may be treated before cleaning, during the cleaning process, after the cleaning processes and any combination thereof. Examples of such articles to be treated include laundry, dishes, carpets, and fabrics.

The term "fabrics" encompasses all kind of fabrics, textiles, fibers, clothes garments, and fabrics used on, e.g., furniture and cars. The term "laundry" refers to already used and/or stained/soiled clothes in need of washing, and is in contrast to newly manufactured fabrics. Washing laundry may be carried out in private households and in commercial and institutional facilities, such as, hospitals, prisons, uniform service companies. Washing of newly manufactured fabrics is mainly done in the textile industry. The fabric or laundry may be made from any suitable material. In preferred embodiments the fabrics and/or laundry are made from cellulosic materials, synthetic materials and/or man-made fibers, or blends thereof. Examples of contemplated cellulosic materials include cotton, viscose, rayon, ramie, linen, lyocell (e.g., TENCEL™, produced by Courtaulds Fibers), or blends thereof, or blends of any of these fibers together with synthetic or man-made fibers (e.g., polyester, polyamid, nylon) or other natural fibers such as wool and silk, such as viscose/cotton blends, lyocell/cotton blends, viscose/wool blends, lyocell/wool blends, cotton/wool blends; flax (linen), ramie and other fabrics and/or laundry based on cellulose fibers, including all blends of cellulosic fibers with other fibers such as wool, polyamide, acrylic and polyester fibers, e.g., viscose/cotton/polyester blends, wool/cotton/polyester blends, flax/cotton blends etc. The fabric and/or laundry may also be a synthetic materials, e.g., consisting of essentially 100% polyester, polyamid, nylon, respectively. The term "wool," means any commercially useful animal hair product, for example, wool from sheep, camel, rabbit, goat, llama, and known as merino wool, Shetland wool, cashmere wool, alpaca wool, mohair etc. and includes wool fibers and animal hair. The method of the invention can be used on wool or animal hair material in the form of top, fiber, yarn, or woven or knitted fabrics.

The treating may include contacting the odor-generating organism(s) or odor-generating compound(s) present in the cleaning machine or cleaning process with the at least one microorganism. Such contacting may include contacting a surface of a machine with the at least one microorganism and/or contacting a process water or cleaning composition used in the cleaning machine with the at least one microorganism.

Contacting means contacting the odor-causing organism and/or odor causing compound with living cells of the at least one microorganism. In another aspect, the invention also includes contacting the odor-causing organism or odor-causing compound with one or more substances derived from the at least one microorganism which has the ability to inhibit odor as described herein. Such substances include, but are not limited to, cell-free supernatants, cell lysates, and/or extracts.

The at least one microorganism may be applied in any suitable form, such as, as a spore or as vegetative cell. The ability to prepare spores and vegetative cells is considered routine in the art. See Tzeng et al., 2008. "Effect of cultivation conditions on spore production from *Bacillus amyloliquefaciens* B128 and its antagonism to *Botrytis elliptica*." *Journal of Applied Microbiology* 104(5): 1275-1282.

Compositions of the invention comprise at least one microorganism as described herein. The microorganisms should be present in effective amounts. The terms "effective amount", "effective concentration" or "effective dosage" are defined herein as the amount, concentration or dosage of one or more odor-controlling microbial strains that can inhibit the malodor caused by the odor causing organism or substances derived therefrom on articles, articles subjected to a cleaning machine or cleaning process, and/or cleaning machines. The actual effective dosage in absolute numbers depends on factors including: the odor causing organisms(s) in question; whether the aim is prevention or reduction of malodor; other ingredients present in the composition, and also the articles and/or cleaning machine in question. In an embodiment an effective dosage of bacteria, e.g., of the strains NRRL B-50141, PTA-7549, or PTA-7543, would be introduced to the detergent at a final concentration of $1 \times 10^3$-$1 \times 10^{11}$ CFU/g of detergent, with a preferred range of $1 \times 10^5$-$1 \times 10^6$ CFU/g of detergent. Effective amounts can be determined by one skilled in the art using routine assays.

The at least one microorganism of the invention and/or substances derived therefrom can be used in combination with or as an ingredient of a washing product, such as detergents and/or fabric softeners in particular, including but not limited to aerosols, powders, solids, creams, etc., for use, e.g., in cleaning machines, cleaning processes and/or articles treated in cleaning machines or cleaning processes, such as, fabrics. Formulations to be applied will include live biocontrol bacterial, e.g., spores or vegetative cells.

An aspect of the present invention also includes cleaning compositions or compositions for use in cleaning machines or cleaning processes which comprise at least one microorganisms described herein and a carrier. The composition may be in the form of a solid, semi-solid, gel, liquid, aerosol, emulsion, and/or powder. In an aspect, the composition comprises a carrier and at least one microorganism or a substance derived therefrom. In another aspect the composition comprises a carrier and at least one species of *Bacillus* or a substance derived therefrom. In another aspect, the composition comprises a carrier and at least one microorganism selected from the group consisting of *Bacillus subtilis, Bacillus amyloliquefaciens, Bacillus licheniformis, Bacillus atrophaeus* and *Bacillus pumilus* or a combination thereof. Most preferably, the species of *Bacillus* is *Bacillus subtilis, Bacillus amyloliquefaciens, Bacillus pumilus*, or a combination thereof. In another embodiment, the composition comprises a carrier and at least one microorganism selected from the group consisting of *Bacillus pumilus* strain NRRL B-50016; *Bacillus amyloliquefaciens* strain PTA-7792; *Bacillus amyloliquefaciens* strain PTA-7543; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus subtilis* strain PTA-7547; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; and *Bacillus licheniformis* strain NRRL B-50015 or a combination thereof. More preferably, the at least one strain of *Bacillus* is selected from the group consisting of *Bacillus pumilus* strain NRRL B-50016; *Bacillus amyloliq-* uefaciens strain PTA-7543; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7791; *Bacillus subtilis* strain NRRL B-50136; *Bacillus amyloliquefaciens* strain NRRL B-50141; and *Bacillus amyloliquefaciens* strain NRRL B-50399 or a combination thereof. Most preferably, the at least one strain of *Bacillus* is selected from the group consisting of *Bacillus amyloliquefaciens* strain PTA-7541; *Bacillus amyloliquefaciens* strain PTA-7543 *Bacillus amyloliquefaciens* strain PTA-7546; *Bacillus amyloliquefaciens* strain PTA-7549; *Bacillus amyloliquefaciens* strain NRRL B-50141; *Bacillus amyloliquefaciens* strain NRRL B-50706; and *Bacillus subtilis* strain NRRL B-50136 or a combination thereof. The compositions may in particular embodiments comprise blends of two or more microorganisms, including at least two, at least three, at least four, and at least five of the microorganisms described herein.

The compositions of the present invention may in an embodiment have a pH in the range of 5-10 and may further include water and/or one or more preservatives. For preservation of compositions comprising *Bacillus* sp., for example, the following preservatives can be useful: chloromethylisothiazolinone/methylisothiazolinone (OMIT/MIT) (Kathon or others); MIT (Neolone or others); 1,2-benzisothiazolin-3-one (BIT) (if allowed in personal care); OMIT/MIT+EDTA; OMIT/MIT+Biodegradable Chelator; MIT+EDTA; MIT+Biodegradable Chelator; BIT+EDTA; BIT+Biodegradable Chelator; Bronopol; 2-Phenoxyethanol; 2-Phenoxyethanol+Biodegradable Chelator; Potassium sorbate (used at low pH); Sodium benzoate (used at low pH); Salt; Glycerol; Propylene Glycol; Essential Oils; Dichlorobenzyl alcohol; Triclosan; Parabens; and 1-Phenoxy-2-propanol and 2-Phenoxy-1-propanol. In an embodiment, the preservative is 2-Phenoxyethanol; 2-Phenoxyethanol+Biodegradable Chelator; Potassium Sorbate (used at low pH); Sodium Benzoate (used at low pH); Salt; Glycerol; Propylene Glycol; or one of more Essential Oils—e.g., white mustard seed, tea tree, rosewood, or some citrus oils. In another embodiment, the preservative is 2-Phenoxyethanol; 2-Phenoxyethanol+Biodegradable Chelator; or Glycerol. Accordingly, an embodiment of the present invention is directed to a composition comprising at least one microorganism which is able to inhibit malodor and a preservative selected from the group consisting of chloromethylisothiazolinone/methylisothiazolinone (OMIT/MIT) (Kathon or others); MIT (Neolone or others); 1,2-benzisothiazolin-3-one (BIT) (if allowed in personal care); OMIT/MIT+EDTA; OMIT/MIT+Biodegradable Chelator; MIT+EDTA; MIT+Biodegradable Chelator; BIT+EDTA; BIT+Biodegradable Chelator; Bronopol; 2-Phenoxyethanol; 2-Phenoxyethanol+Biodegradable Chelator; Potassium sorbate (used at low pH); Sodium benzoate (used at low pH); Salt; Glycerol; Propylene Glycol; Essential Oils; Dichlorobenzyl alcohol; Triclosan; Parabens; and 1-Phenoxy-2-propanol and 2-Phenoxy-1-propanol. In an embodiment, the preservative is 2-Phenoxyethanol; 2-Phenoxyethanol+Biodegradable Chelator; Potassium Sorbate (used at low pH); Sodium Benzoate (used at low pH); Salt; Glycerol; Propylene Glycol; or one of more Essential Oils—e.g., white mustard seed, tea tree, rosewood, or some citrus oils, 2-Phenoxyethanol; 2-Phenoxyethanol+Biodegradable Chelator; or Glycerol, and wherein the composition is a liquid, solid or gel composition.

In one preferred aspect, the invention provides a composition adapted for application to the interior of a cleaning machine (e.g., laundry washing machine or dish washing machine). A composition of the invention may be in solid or liquid form. The composition may be a concentrate to be diluted, rehydrated and/or dissolved in a solvent, including water, before use. The composition may also be a ready-to-use (in-use) composition. The composition may furthermore be an active cleaning base ingredient to be incorporated into other cleaning or washing compositions.

In one embodiment, the composition is adapted for delivery to a washing machine to prevent fouling by bacterial species capable of causing laundry malodor. In another embodiment, the composition is further adapted for delivery to a washing machine by applications which include, but are not limited to, solid, semi-solid, gel, liquid, aerosol, emulsion, and/or powder applications alone and/or in combination with liquid, solid, semi-solid, aerosol, emulsion, and/or gel detergents, alone and/or in combination with liquid, solid, semi-solid, aerosol, emulsion, and/or gel fabric softeners, and/or alone and/or in combination with any other laundry and/or washing maching additive.

In one aspect, the invention provides a composition adapted for application to a fabric. The composition adapted for delivery to a fabric may be in the form of a solid, semi-solid, gel, liquid, aerosol, emulsion, and/or powder, as a treatment for fabrics to prevent fouling by bacterial species capable of causing laundry malodor. In another embodiment, the composition is adapted for delivery to a fabric by applications which include, but are not limited to, solid, semi-solid, gel, liquid, aerosol, emulsion, and/or powder applications alone and/or in combination with liquid, solid, semi-solid, aerosol, emulsion, and/or gel detergents, alone and/or in combination with liquid, solid, semi-solid, aerosol, emulsion, and/or gel fabric softeners, and/or alone and/or in combination with any other laundry and/or washing maching additive.

When used in a cleaning compositions, the composition may comprise one or more additional cleaning composition ingredients, such as, surfactants and/or optionally other active ingredients, such as enzymes.

The surfactants may be non-ionic including semi-polar and/or anionic and/or cationic and/or zwitterionic. The surfactant(s) should cause as little harm to the bacteria culture's activity as possible. The surfactants may be present in the composition at a level of from, e.g., 0.01% to 60% by weight.

The composition may contain from about 0 to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

The composition usually contains from about 0 to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

Water soluble anionic surfactants are preferred. Examples of suitable water soluble anionic surfactants include those selected from the group consisting of alkyl sulfates, alkyl ether sulfates, alkyl amido ether sulfates, alkyl aryl polyether sulfates, alkyl aryl sulfates, alkyl aryl sulfonates, monoglyceride sulfates, alkyl sulfonates, alkyl amide sulfonates, alkyl aryl sulfonates, benzene sulfonates, toluene sulfonates, xylene sulfonates, cumene sulfonates, alkyl benzene sulfonates, alkyl diphenyloxide sulfonate, alpha-olefin sulfonates, alkyl naphthalene sulfonates, paraffin sulfonates, lignin sulfonates, alkyl sulfosuccinates, ethoxylated sulfosuccinates, alkyl ether sulfosuccinates, alkylamide sulfosuccinates, alkyl sulfosuccinamate, alkyl sulfoacetates, alkyl phosphates, phosphate ester, alkyl ether phosphates, acyl sarconsinates, acyl isethionates, N-acyl taurates, N-acyl-N-alkyltaurates, and alkyl carboxylates. Examples of preferred water soluble anionic surfactants include sodium dodecyl sulfate (sodium lauryl sulfate), sodium laureth sulfate (sodium lauryl ether sulfate), sodium dodecyl benzene sulfonate, disodium octyl sulfosuccinate, sodium butyl naphthalene sulfonate, ethoxylated sodium lauryl sulfosuccinate, sodium stearate, and sodium lauroyl sarcoside, or a mixture of two or more. Examples of anionic surfactants are also mentioned in WO 2007/076337 (see page 7, line 8 to page 9, line 3—which is hereby incorporated by reference).

The nonionic surfactant may preferably be a water insoluble nonionic surfactant or a water soluble nonionic surfactant, or mixtures thereof. Examples of suitable nonionic surfactants are given below. Examples of suitable water insoluble nonionic surfactants include alkyl and aryl: glycerol ethers, glycol ethers, ethanolamides, sulfonylamides, alcohols, amides, alcohol ethoxylates, glycerol esters, glycol esters, ethoxylates of glycerol ester and glycol esters, sugar-based alkyl polyglycosides, polyoxyethylenated fatty acids, alkanolamine condensates, alkanolamides, tertiary acetylenic glycols, polyoxyethylenated mercaptans, carboxylic acid esters, and polyoxyethylenated polyoxyproylene glycols. Also included are EO/PO block copolymers (EO is ethylene oxide, PO is propylene oxide), EO polymers and copolymers, polyamines, and polyvinylpyrrolidones. Water soluble nonionic surfactants typically have a higher ethylene oxide content in the hydrophilic region of the surfactant in comparison to water insoluble nonionic surfactants. In an embodiment the water soluble nonionic surfactant is a linear primary, or secondary or branched alcohol ethoxylate having the formula: $RO(CH_2CH_2O)_nH$, wherein R is the hydrocarbon chain length and n is the average number of moles of ethylene oxide. In a preferred embodiment R is linear primary or branched secondary hydrocarbon chain length in the range from C9 to C16 and n ranges from 6 to 13. Especially preferred is the alcohol ethoxylate where R is linear C9-C11 hydrocarbon chain length, and n is 6. Examples of commercially available water soluble nonionic alcohol ethoxylate surfactants include NEODOL™ 91-6, TOMADOL™ 91-6, or BIO-SOFT™ N23-6.5. Examples of non-ionic surfactants are also mentioned in WO 2007/076337 (see page 9, line 5 to page 12, line 14—which is hereby incorporated by reference).

Due to the cost of preparing effective multi-enzyme compositions, adding at least one microorganism (e.g. bacteria) as an active odor removing ingredient may be a good and/or cost efficient alternative to compositions comprising, e.g., mono-component enzymes. Microbial cultures (e.g., bacterial cultures, such as natural bacterial cultures or genetically modified bacterial cultures via classical and/or directed mutagenesis) can be used to supply enzymes in culture and produce enzymes, including on demand in response to the presence of certain compounds. One or more microbial cultures can, among other things, produce one or more enzymes to produce a cleaning effect, to completely degrade a compound and/or use the components and energy from the enzymatic action to produce more bacteria. A bacterial culture of the invention may also advantageously be used to at least partly substitute enzymes in washing, removing odor, or cleaning compositions. In an embodiment the composition comprises from 0.1-90 wt-% culture, preferably 0.5-50 wt.-% culture, especially from 1-10 wt-% culture of the invention.

One or more enzymes may be present in a composition of the invention. Especially contemplated enzymes include proteases, alpha-amylases, cellulases, lipases, phospholipases, peroxidases/oxidases, pectate lyases, and mannanases, or mixtures thereof.

Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583. Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274. Preferred commercially available protease enzymes include ALCALASE™, SAVINASE™, PRIMASE™, DURALASE™, DYRAZYM™, ESPERASE™' EVERLASE™, POLARZYME™ and KANNASE™, LIQUANASE™ (Novozymes A/S), MAXATASE™, MAXACAL™, MAXAPEM™, PROPERASE™, PURAFECT™, PURAFECT OxP™, FN2™, and FN3™ (Genencor International Inc.).

Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta* 1131: 253-360), *B. stearothermophilus* (JP 64/744992) or *B. pumilus* (WO 91/16422). Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202. Preferred commercially available lipase enzymes include LIPOLASE™ and LIPOLASE ULTRA™, LIPOZYME™, and LIPEX™ (Novozymes A/S).

Cutinases classified in EC 3.1.1.74 may also be used. Cutinases are enzymes which are able to degrade cutin. The cutinase used according to the invention may be of any origin. Preferably cutinases are of microbial origin, in particular of bacterial, of fungal or of yeast origin. In a preferred embodiment, the cutinase is derived from a strain of *Aspergillus*, in particular *Aspergillus oryzae*, a strain of *Alternaria*, in particular *Alternaria brassiciola*, a strain of *Fusarium*, in particular *Fusarium solani*, *Fusarium solani pisi*, *Fusarium roseum culmorum*, or *Fusarium roseum*

*sambucium*, a strain of *Helminthosporum*, in particular *Helminthosporum sativum*, a strain of *Humicola*, in particular *Humicola insolens*, a strain of *Pseudomonas*, in particular *Pseudomonas mendocina*, or *Pseudomonas putida*, a strain of *Rhizoctonia*, in particular *Rhizoctonia solani*, a strain of *Streptomyces*, in particular *Streptomyces scabies*, or a strain of *Ulocladium*, in particular *Ulocladium consortiale*. In a most preferred embodiment the cutinase is derived from a strain of *Humicola insolens*, in particular the strain *Humicola insolens* DSM 1800. *Humicola insolens* cutinase is described in WO 96/13580 which is hereby incorporated by reference. The cutinase may be a variant, such as one of the variants disclosed in WO 00/34450 and WO 01/92502, which are hereby incorporated by reference. Preferred cutinase variants include variants listed in Example 2 of WO 01/92502, which is hereby specifically incorporated by reference. Preferred commercial cutinases include NOVOZYM™ 51032 (available from Novozymes A/S, Denmark).

Phospholipases are classified as EC 3.1.1.4 and/or EC 3.1.1.32. As used herein, the term phospholipase is an enzyme which has activity towards phospholipids. Phospholipids, such as lecithin or phosphatidylcholine, consist of glycerol esterified with two fatty acids in an outer (sn-1) and the middle (sn-2) positions and esterified with phosphoric acid in the third position; the phosphoric acid, in turn, may be esterified to an amino-alcohol. Phospholipases are enzymes which participate in the hydrolysis of phospholipids. Several types of phospholipase activity can be distinguished, including phospholipases $A_1$ and $A_2$ which hydrolyze one fatty acyl group (in the sn-1 and sn-2 position, respectively) to form lysophospholipid; and lysophospholipase (or phospholipase B) which can hydrolyze the remaining fatty acyl group in lysophospholipid. Phospholipase C and phospholipase D (phosphodiesterases) release diacyl glycerol or phosphatidic acid respectively. The term phospholipase includes enzymes with phospholipase activity, e.g., phospholipase A ($A_1$ or $A_2$), phospholipase B activity, phospholipase C activity or phospholipase D activity. The term "phospholipase A" used herein in connection with an enzyme of the invention is intended to cover an enzyme with Phospholipase $A_1$ and/or Phospholipase $A_2$ activity. The phospholipase activity may be provided by enzymes having other activities as well, such as, e.g., a lipase with phospholipase activity. The phospholipase activity may, e.g., be from a lipase with phospholipase side activity. In other embodiments of the invention the phospholipase enzyme activity is provided by an enzyme having essentially only phospholipase activity and wherein the phospholipase enzyme activity is not a side activity.

The phospholipase may be of any origin, e.g., of animal origin (such as, e.g., mammalian), e.g., from pancreas (e.g., bovine or porcine pancreas), or snake venom or bee venom. Preferably the phospholipase may be of microbial origin, e.g., from filamentous fungi, yeast or bacteria, such as the genus or species *Aspergillus*, e.g., *A. niger, Dictyostelium*, e.g., *D. discoideum; Mucor*, e.g., *M. javanicus, M. mucedo, M. subtilissimus; Neurospora*, e.g., *N. crassa; Rhizomucor*, e.g., *R. pusillus; Rhizopus*, e.g., *R. arrhizus, R. japonicus, R. stolonifer, Scierotinia*, e.g., *S. libertiana; Trichophyton*, e.g., *T. rubrum; Whetzelinia*, e.g., *W. scierotiorum; Bacillus*, e.g., *B. megaterium, B. subtilis; Citrobacter*, e.g., *C. freundii; Enterobacter*, e.g., *E. aerogenes, E. cloacae; Edwardsiella, E. tarda; Erwinia*, e.g., *E. herbicola; Escherichia*, e.g., *E. coli; Klebsiella*, e.g., *K. pneumoniae; Proteus*, e.g., *P. vulgaris; Providencia*, e.g., *P. stuartii; Salmonella*, e.g., *S. typhimurium; Serratia*, e.g., *S. liquefasciens, S. marcescens; Shigella*, e.g., *S. flexneri; Streptomyces*, e.g., *S. violeceoruber, Yersinia*, e.g., *Y. enterocolitica*. Thus, the phospholipase may be fungal, e.g., from the class Pyrenomycetes, such as the genus *Fusarium*, such as a strain of *F. culmorum, F. heterosporum, F. solani*, or a strain of *F. oxysporum*. The phospholipase may also be from a filamentous fungus strain within the genus *Aspergillus*, such as a strain of *Aspergillus awamori, Aspergillus foetidus, Aspergillus japonicus, Aspergillus niger* or *Aspergillus oryzae*. Preferred phospholipases are derived from a strain of *Humicola*, especially *Humicola lanuginosa*. The phospholipase may be a variant, such as one of the variants disclosed in WO 00/32758, which are hereby incorporated by reference. Preferred phospholipase variants include variants listed in Example 5 of WO 00/32758, which is hereby specifically incorporated by reference. In another preferred embodiment the phospholipase is one described in WO 04/111216, especially the variants listed in the table in Example 1. In another preferred embodiment the phospholipase is derived from a strain of *Fusarium*, especially *Fusarium oxysporum*. The phospholipase may be the one concerned in WO 98/026057 displayed in SEQ ID NO: 2 derived from *Fusarium oxysporum* DSM 2672, or variants thereof. In a preferred embodiment of the invention the phospholipase is a phospholipase $A_1$ (EC. 3.1.1.32). In another preferred embodiment of the invention the phospholipase is a phospholipase $A_2$ (EC.3.1.1.4.). Examples of commercial phospholipases include LECITASE™ and LECITASE™ ULTRA, YIELSMAX, or LIPOPAN F (available from Novozymes A/S, Denmark).

Suitable amylases (alpha and/or beta) include those of bacterial or fungal origin. Chemically modified or protein engineered mutants are included. Amylases include, for example, alpha-amylases obtained from *Bacillus*, e.g., a special strain of *B. licheniformis*, described in more detail in GB 1,296,839, or the *Bacillus* sp. strains disclosed in WO 95/026397 or WO 00/060060. Examples of useful amylases are the variants described in WO 94/02597, WO 94/18314, WO 96/23873, WO 97/43424, WO 01/066712, WO 02/010355, WO 02/031124 and WO 2006/002643 (which references all incorporated by reference. Commercially available amylases are DURAMYL™, TERMAMYL™, TERMAMYL ULTRA™, NATALASE™ STAINZYME™, STAINZYME ULTRA™, FUNGAMYL™ and BAN™ (Novozymes A/S), RAPIDASE™ and PURASTAR™ (from Genencor International Inc.).

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Thielavia terrestris, Myceliophthora thermophila*, and *Fusarium oxysporum* disclosed in U.S. Pat. No. 4,435,307, U.S. Pat. No. 5,648,263, U.S. Pat. No. 5,691,178, U.S. Pat. No. 5,776,757, WO 89/09259, WO 96/029397, and WO 98/012307. Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and WO 1999/001544. Commercially available cellulases include CELLUZYME™, CELLUCLAST™, CAREZYME™, ENDOLASE™, RENOZYME™ (Novozymes A/S), CLAZINASE™ and PURADAX HA™, ACCELERASE™ 1000 (Genencor International Inc.), and KAC-500(B)™ (Kao Corporation).

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ and Novozym™ 51004 (Novozymes A/S).

Pectate lyases (also called polygalacturonate lyases) may also be used. Examples of pectate lyases include pectate lyases that have been cloned from different bacterial genera such as *Erwinia, Pseudomonas, Klebsiella* and *Xanthomonas*, as well as from *Bacillus subtilis* (Nasser et al., 1993, *FEBS* Letts. 335:319-326) and *Bacillus* sp. YA-14 (Kim et al., 1994, *Biosci. Biotech. Biochem.* 58: 947-949). Purification of pectate lyases with maximum activity in the pH range of 8-10 produced by *Bacillus pumilus* (Dave and Vaughn, 1971, *J. Bacteriol.* 108: 166-174), *B. polymyxa* (Nagel and Vaughn, 1961, *Arch. Biochem. Biophys.* 93: 344-352), *B. stearothermophilus* (Karbassi and Vaughn, 1980, *Can. J. Microbiol.* 26: 377-384), *Bacillus* sp. (Hasegawa and Nagel, 1966, *J. Food Sci.* 31: 838-845) and *Bacillus* sp. RK9 (Kelly and Fogarty, 1978, *Can. J. Microbiol.* 24: 1164-1172) have also been described. Any of the above, as well as divalent cation-independent and/or thermostable pectate lyases, may be used in practicing the invention. In preferred embodiments, the pectate lyase comprises the amino acid sequence of a pectate lyase disclosed in Heffron et al., 1995, *Mol. Plant-Microbe Interact.* 8: 331-334 and Henrissat et al., 1995, *Plant Physiol.* 107: 963-976. Specifically contemplated pectate lyases are disclosed in WO 99/27083 and WO 99/27084. Other specifically contemplated pectate lyases derived from *Bacillus licheniformis* is disclosed as SEQ ID NO: 2 in U.S. Pat. No. 6,284,524 (which document is hereby incorporated by reference). Specifically contemplated pectate lyase variants are disclosed in WO 02/006442, especially the variants disclosed in the Examples in WO 02/006442 (which document is hereby incorporated by reference). Examples of commercially available alkaline pectate lyases include BIOPREP™ and SCOURZYME™ L from Novozymes A/S, Denmark.

Examples of mannanases (EC 3.2.1.78) include mannanases of bacterial and fungal origin. In a specific embodiment the mannanase is derived from a strain of the filamentous fungus genus *Aspergillus*, preferably *Aspergillus niger* or *Aspergillus aculeatus* (WO 94/25576). WO 93/24622 discloses a mannanase isolated from *Trichoderma reesei*. Mannanases have also been isolated from several bacteria, including *Bacillus* organisms. For example, Talbot et al., 1990, *Appl. Environ. Microbiol.* 56(11): 3505-3510 describes a beta-mannanase derived from *Bacillus stearothermophilus*. Mendoza et al., 1994, *World J. Microbiol. Biotech.* 10(5): 551-555 describes a beta-mannanase derived from *Bacillus subtilis*. JP-A-03047076 discloses a beta-mannanase derived from *Bacillus* sp. JP-A-63056289 describes the production of an alkaline, thermostable beta-mannanase. JP-A-63036775 relates to the *Bacillus* microorganism FERM P-8856 which produces beta-mannanase and beta-mannosidase. JP-A-08051975 discloses alkaline beta-mannanases from alkalophilic *Bacillus* sp. AM-001. A purified mannanase from *Bacillus amyloliquefaciens* is disclosed in WO 97/11164. WO 91/18974 describes a hemicellulase such as a glucanase, xylanase or mannanase active. Contemplated are the alkaline family 5 and 26 mannanases derived from *Bacillus agaradhaerens, Bacillus licheniformis, Bacillus halodurans, Bacillus clausii, Bacillus* sp., and *Humicola insolens* disclosed in WO 99/64619. Especially contemplated are the *Bacillus* sp. mannanases concerned in the Examples in WO 99/64619 which document is hereby incorporated by reference. Examples of commercially available mannanases include MANN-AWAY™ available from Novozymes A/S Denmark.

Enzymes may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

In addition to surfactants and/or enzymes, other contemplated ingredients that may be included in the cleaning compositions include salts, buffer salts, hydrotropes, preservatives, fillers, builders, complexing agents, polymers, stabilizers, perfumes, biostimulants or nutrients, dispersants, anti-microbial agents, fragrances, dyes, and biocides, or combinations of one or more thereof.

The salts or buffer salts may be any known inorganic salt, but is preferably a salt selected from the group consisting of alkali metal salts of nitrates, acetates, chlorides, bromides, iodides, sulfates, hydroxides, carbonates, hydrogen carbonates, (also called bicarbonates), phosphates, sulfides, and sulfites; ammonium salts of nitrates, acetates, chlorides, bromides, iodides, sulfates, hydroxides, carbonates, hydrogen carbonates (also called bicarbonates), phosphates, sulfides, and sulfites; alkaline earth metal salts of nitrates, chlorides, bromides, iodides, sulfates, sulfides, and hydrogen carbonates; manganese, iron, copper, and zinc salts of nitrates, acetates, chlorides, bromides, iodides, and sulfates; citrates and borates.

Especially contemplated are carbonates or bicarbonates, in particular selected from the group consisting of sodium carbonate and sodium bicarbonate, or a mixture thereof. In a specific embodiment the ratio between sodium carbonate and sodium bicarbonate is between 1:10 to 10:1.

The total amount of salts and/or buffer salts is preferably between 0.8 to 8 wt. %, preferably 1-5 wt. %, more preferably around 2 wt. % of the final in-use cleaning composition.

The term "hydrotrope" generally means a compound with the ability to increase the solubilities, preferably aqueous solubilities, of certain slightly soluble organic compounds. Examples of hydrotropes include sodium xylene sulfonate (SXS) and sodium cumene sulfonate (SCS).

The composition may contain a metal chelating agent such as carbonates, bicarbonates, and sesquicarbonates.

The composition may comprise a solvent such as water or an organic solvent such as isopropyl alcohol or a glycol ether.

The composition may also contain 0-65% of a builder or complexing agent such as zeolite, phosphates, such as diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, silicates, such as soluble silicates, metasilicates, layered silicates (e.g. SKS-6 from Hoechst).

The composition may comprise one or more polymers. Examples are carboxymethylcellulose, poly(vinylpyrrolidone), poly (ethylene glycol), poly(vinyl alcohol), poly (vinylpyridine-N-oxide), poly(vinylimidazole), polycarboxylates such as polyacrylates, maleic/acrylic acid copolymers and lauryl methacrylate/acrylic acid copolymers.

In particular for detergent compositions, the composition may also contain other conventional detergent ingredients such as, e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes. In an embodiment the solid composition contains the following constitutes: hydrotropes, anionic or nonionic surfactants, builders, carbonates for pH control and metal chelation, solvents, fillers, dye, perfume, and fluorescent whitening agent.

Essential oils may also be included, such as, Rosewood, Celery seed, Frankincense, Ylang ylang, Cedarwood, Lime, Orange, Petitgrain, Bergamot, Lemon, Grapefruit, Mandarin, Myrrh, Coriander, Pumpkin, Cypress, Lemongrass, Palmarosa, Citronella, Carrot seed, Eucalyptus, Fennel, Wintergreen, Juniper, French lavender, Tasmanian lavender, Macadamia, Tea tree, Cajuput, Niaouli, Peppermint, Spearmint, Basil, Evening primrose, Marjoram, Oregano, Geranium, Aniseed, Bay, Pine, Black pepper, Patchouli, Apricot kernel, Sweet almond, Rosemary, Sage, Clary sage, Sandalwood, Clove, Thyme, Vetiver, and Ginger. Additional guidance regarding selection of appropriate essential oils may be found in Hammer, K. A., et al., *J. Applied Microbiol.*, 86:985-990 (1999), incorporated herein by reference for its disclosure of essential oils/plant extracts and their antimicrobial activity.

The present invention is described, at least in part, by the following numbered paragraphs:

1. A method of inhibiting or preventing the production of laundry malodor caused by at least one malodor causing bacteria or at least one bacteria capable of causing malodor, comprising contacting a fabric or a laundry washing machine with at least one microorganism capable of inhibiting or preventing the production of malodor caused by the at least one malodor causing bacteria or the at least one bacteria capable of causing malodor.

2. The method of paragraph 1, wherein the method comprises contacting the at least one malodor causing bacteria or at least one bacteria capable of causing laundry malodor.

3. The method of paragraph 1 or 2, wherein the method comprises contacting an odor generating compound derived from the at least one malodor causing bacteria or at least one bacteria capable of causing odor.

4. The method of any of paragraphs 1-3, wherein the contacting comprises administering at least one microorganism to a laundry washing machine.

5. The method of any of paragraphs 1-4, wherein the contacting is done during a washing process.

6. The method of any of paragraphs 1-5, wherein the contacting is done to a new washing machine.

7. The method of any of paragraphs 1-6, wherein the contacting is done to a washing machine following one or more uses of said washing machine.

8. The method of any of paragraphs 1-7, wherein the at least one microorganism is at least one species of *Bacillus*.

9. The method of paragraph 8, wherein the at least one species of *Bacillus* is selected from the group consisting of *Bacillus subtilis*, *Bacillus amyloliquefaciens*, *Bacillus pumilus*, *Bacillus licheniformis*, *Bacillus atrophaeus*, and combinations thereof.

10. The method of paragraph 8 or 9, wherein the at least one species of *Bacillus* is selected from the group consisting of *Bacillus pumilus* strain NRRL B-50016; *Bacillus amyloliquefaciens* strain NRRL B-50017, *Bacillus amyloliquefaciens* strain PTA-7792; *Bacillus amyloliquefaciens* strain PTA-7543; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus subtilis* strain PTA-7547; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; *Bacillus amyloliquefaciens* strain NRRL B-50706; and combinations thereof.

11. The method of any of paragraphs 1-3, wherein the at least one malodor causing bacteria or at least one bacteria capable of causing malodor is at least one bacterial species selected from the group consisting of *Bacillus amyloliquefaciens*, *Acinetobacter junii*, *Bacillus subtilis*, *Janibacter melois*, *Sphingobium ummariense*, *Sphingomonas panni*, Sphingomonadaceae sp., *Actinobacter tandoii*, *Junibacter melonis*, *Curtobacterium flaccumfaciens*, *Flavobacterium denitrificans*, *Staphylococcus epidermidis*, *Escherichia coli*, *Leclercia adecarboxylata*, *Enterobacter* sp., *Cronobacter sakazakii*, *Bacillus megaterium*, *Sphingobacterium faecium*, *Enterobacter cloacae*, *Pseudomonas veronii*, *Microbacterium luteolum*, *Morganella morganii*, *Bacillus cereus*, *Pseudomonas* sp., *Pseudomonas-marginalis*, *Citrobacter* sp., *Escherichia coli* strain JCLys5, *Roseomonas aquatic*, *Pseudomonas panipatensis*, *Brevibacillus subtilis subtilis*, *Micrococcus luteus*, *Bacillus pumilus*, *Ralstonia eutropha*, *Caulobacter fusiformis*, *Stenotrophomonas maltophilia*, *Rhodococcus opacus*, *Breviundimonas intermedia*, *Agrobacterium tumefaciens*, and combinations thereof.

12. A method of inhibiting or preventing the production of laundry malodor caused by *Bacillus amyloliquefaciens* comprising contacting a fabric or a laundry washing machine with at least one strain of *Bacillus* is capable of inhibiting or preventing the production of malodor caused by *Bacillus amyloliquefaciens* wherein the at least one strain of *Bacillus* is selected from the group consisting of *Bacillus subtilis* strain NRRL B-50136; *Bacillus amyloliquefaciens* strain PTA-7541; *Bacillus amyloliquefaciens* strain PTA-7543; *Bacillus amyloliquefaciens* strain PTA-7546; *Bacillus amyloliquefaciens* strain PTA-7791; *Bacillus amyloliquefaciens* strain NRRL B-50399; *Bacillus amyloliquefaciens* strain NRRL B-50017; *Bacillus amyloliquefaciens* strain NRRL B-50141; and combinations thereof.

13. The method of paragraph 12, wherein the at least one strain of *Bacillus* is selected from the group consisting of *Bacillus amyloliquefaciens* strain PTA-7541; *Bacillus amyloliquefaciens* strain PTA-7546; *Bacillus amyloliquefaciens* strain PTA-7791; *Bacillus amyloliquefaciens* strain NRRL B-50399; *Bacillus amyloliquefaciens* strain NRRL B-50017; *Bacillus amyloliquefaciens* strain NRRL B-50141; *Bacillus subtilis* strain NRRL B-50136; and combinations thereof.

14. The method of paragraph 12 or 13, where the at least one strain of *Bacillus* is selected from the group consisting of *Bacillus subtilis* strain NRRL B-50136; *Bacillus amyloliquefaciens* strain NRRL B-50017; *Bacillus amyloliquefaciens* strain NRRL B-50141; *Bacillus amyloliquefaciens* strain NRRL B-50399; and combinations thereof.

15. A method of inhibiting or preventing the production of laundry malodor caused by *Acinetobacter junii* comprising contacting a fabric or a laundry washing machine with at least one strain of *Bacillus* capable of inhibiting or preventing the production of malodor caused by *Acinetobacter junii* wherein the at least one strain of *Bacillus* is selected from the group consisting of *Bacillus amyloliquefaciens* strain PTA-7549; *Bacillus amyloliquefaciens* strain NRRL B-50399; and combinations thereof.

16. The method of paragraph 15, where the at least one strain of *Bacillus* is *Bacillus amyloliquefaciens* strain NRRL B-50399.

17. A method of inhibiting or preventing the production of laundry malodor caused by *Bacillus subtilis* comprising contacting a fabric or a laundry washing machine with at least one strain of *Bacillus* capable of inhibiting or preventing the production of malodor caused by *Bacillus subtilis* wherein the at least one strain of *Bacillus* is selected from the group consisting of *Bacillus subtilis* strain NRRL B-50136; *Bacillus amyloliquefaciens* strain PTA-7543; *Bacillus amyloliquefaciens* strain NRRL B-50017; *Bacillus amyloliquefaciens* strain NRRL B-50141; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus amyloliquefaciens* strain NRRL B-50399; and combinations thereof. 18. The method of paragraph 17, where the at least one strain of *Bacillus* is selected from the group consisting of *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus amyloliquefaciens* strain NRRL B-50399; and combinations thereof.

19. The method of paragraph 17 or 18, where the at least one strain of *Bacillus* is selected from the group consisting of *Bacillus amyloliquefaciens* strain PTA-7793; *Bacillus amyloliquefaciens* strain PTA-7791; and combinations thereof.

20. A method of inhibiting or preventing the production of laundry malodor caused by *Janibacter melonis* comprising contacting a fabric or a laundry washing machine with at least one strain of *Bacillus* capable of inhibiting or preventing the production of malodor caused by *Janibacter melonis* wherein the at least one strain of *Bacillus* is selected from the group consisting of *Bacillus subtilis* strain NRRL B-50136; *Bacillus licheniformis* strain NRRL B-50014; *Bacillus pumilus* strain NRRL B-50016; *Bacillus amyloliquefaciens* strain NRRL B-50017; *Bacillus amyloliquefaciens* strain NRRL B-50141; *Bacillus amyloliquefaciens* strain PTA-7543; *Bacillus amyloliquefaciens* strain PTA-7541; *Bacillus amyloliquefaciens* strain PTA-7545; *Bacillus amyloliquefaciens* strain PTA-7546; *Bacillus subtilis* strain PTA-7547; *Bacillus amyloliquefaciens* strain PTA-7793; *Bacillus amyloliquefaciens* strain PTA-7791; and combinations thereof.

21. The method of paragraph 20, wherein the at least one strain of *Bacillus* is selected from the group consisting of *Bacillus subtilis* strain NRRL B-50136; *Bacillus pumilus* strain NRRL B-50016; *Bacillus amyloliquefaciens* strain NRRL B-50017; *Bacillus amyloliquefaciens* strain NRRL B-50141; *Bacillus amyloliquefaciens* strain PTA-7791; and combinations thereof.

22. The method of paragraph 20 or 21, where the at least one strain of *Bacillus* is *Bacillus subtilis* strain NRRL B-50136; *Bacillus pumilus* strain NRRL B-50016; and combinations thereof.

23. A method of inhibiting or preventing the production of laundry malodor caused by *Sphingobium ummariense* comprising contacting a fabric or a laundry washing machine with at least one strain of *Bacillus* capable of inhibiting or preventing the production of malodor caused by *Sphingobium ummariense* wherein the at least one strain of *Bacillus* is selected from the group consisting of *Bacillus pumilus* strain NRRL B-50016; *Bacillus amyloliquefaciens* strain NRRL B-50018; *Bacillus amyloliquefaciens* strain PTA-7541; *Bacillus amyloliquefaciens* strain PTA-7549; and combinations thereof.

24. The method of paragraph 23, wherein the at least one strain of *Bacillus* is selected from the group consisting of *Bacillus amyloliquefaciens* strain NRRL B-50018; *Bacillus amyloliquefaciens* strain PTA-7541; *Bacillus amyloliquefaciens* strain PTA-7549; and combinations thereof.

25. The method of paragraph 23 or 24, where the at least one strain of *Bacillus* is *Bacillus amyloliquefaciens* strain PTA-7549.

26. A method of inhibiting or preventing the production of laundry malodor caused by *Sphingomonas panni* comprising contacting a fabric or a laundry washing machine with at least one strain of *Bacillus* capable of inhibiting or preventing the production of malodor caused by *Sphingomonas panni* wherein the at least one strain of *Bacillus* is *Bacillus amyloliquefaciens* strain NRRL B-50141; *Bacillus amyloliquefaciens* strain NRRL B-50017; and combinations thereof.

27. A method of inhibiting or preventing the production of laundry malodor caused by bacteria from the family Sphingomonadaceae comprising contacting a fabric or a laundry washing machine with at least one strain of *Bacillus* capable of inhibiting or preventing the production of malodor caused by bacteria from the family Sphingomonadaceae wherein the at least one strain of *Bacillus* is selected from the group consisting of *Bacillus amyloliquefaciens* strain NRRL B-50141; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; and combinations thereof.

28. The method of paragraph 27, wherein the at least one strain of *Bacillus* is selected from the group consisting of *Bacillus amyloliquefaciens* strain PTA-7541; *Bacillus amyloliquefaciens* strain PTA-7544; and combinations thereof. 29. The method of paragraph 27 or 28, where the at least one strain of *Bacillus* is *Bacillus amyloliquefaciens* strain PTA-7541.

30. A method of inhibiting or preventing the production of laundry malodor caused by *Acinetobacter tandoii* comprising contacting a fabric or a laundry washing machine with at least one strain of *Bacillus* capable of inhibiting or preventing the production of malodor caused by *Acinetobacter tandoii* wherein the at least one strain of *Bacillus* is *Bacillus amyloliquefaciens* strain PTA-7549.

31. A method of inhibiting or preventing the production of laundry malodor caused by *Curtobacterium flaccumfaciens* comprising contacting a fabric or a laundry washing machine with at least one strain of *Bacillus* capable of inhibiting or preventing the production of malodor caused by *Curtobacterium flaccumfaciens* wherein the at least one strain of *Bacillus* is selected from the group consisting of *Bacillus subtilis* strain NRRL B-50136; *Bacillus pumilus* strain NRRL B-50016; *Bacillus amyloliquefaciens* strain PTA-7541; *Bacillus subtilis* strain PTA-7547; and combinations thereof.

32. The method of paragraph 31, wherein the at least one strain of *Bacillus* is selected from the group consisting of *Bacillus pumilus* strain NRRL B-50016; *Bacillus amyloliquefaciens* strain PTA-7541; *Bacillus subtilis* strain PTA-7547; and combinations thereof.

33. The method of paragraph 31 or 32, where the at least one strain of *Bacillus* is selected from the group consisting of *Bacillus amyloliquefaciens* strain PTA-7541; *Bacillus subtilis* strain PTA-7547; and combinations thereof.

34. A method of inhibiting or preventing the production of laundry malodor caused by *Flavobacterium denitrificans* comprising contacting a fabric or a laundry washing machine with at least one strain of *Bacillus* capable of inhibiting or preventing the production of malodor caused by *Flavobacterium denitrificans* wherein the at least one strain of *Bacillus* is *Bacillus subtilis* strain NRRL B-50136.

35. A method of inhibiting or preventing the production of laundry malodor caused by *Staphylococcus epidermidis* comprising contacting a fabric or a laundry washing machine with at least one strain of *Bacillus* capable of inhibiting or preventing the production of malodor caused by *Staphylococcus epidermidis* wherein the at least one strain of *Bacillus* is selected from the group consisting of *Bacillus pumilus* strain NRRL B-50016; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50017; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

36. The method of paragraph 35, wherein the at least one strain of *Bacillus* is selected from the group consisting of *Bacillus pumilus* strain NRRL B-50016; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50399; *Bacillus licheniformis* strain NRRL B-50015; and combinations thereof.

37. The method of paragraph 35 or 36, where the at least one strain of *Bacillus* is selected from the group consisting of *Bacillus amyloliquefaciens* strain NRRL B-50018; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7793; *Bacillus amyloliquefaciens* strain PTA-7790; *Bacillus amyloliquefaciens* strain PTA-7791; *Bacillus amyloliquefaciens* strain NRRL B-50399; *Bacillus licheniformis* strain NRRL B-50015; and combinations thereof.

38. A method of inhibiting or preventing the production of laundry malodor caused by *Escherichia coli* comprising contacting a fabric or a laundry washing machine with at least one strain of *Bacillus* capable of inhibiting or preventing the production of malodor caused by *Escherichia coli* wherein the at least one strain of *Bacillus* is selected from the group consisting of *Bacillus pumilus* strain NRRL B-50016; *Bacillus amyloliquefaciens* strain NRRL B-50017 *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

39. A method of inhibiting or preventing the production of laundry malodor caused by *Leclercia adecarboxylata* comprising contacting a fabric or a laundry washing machine with at least one strain of *Bacillus* capable of inhibiting or preventing the production of malodor caused by *Leclercia adecarboxylata* wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

40. A method of inhibiting or preventing the production of laundry malodor caused by *Enterobacter* sp. comprising contacting a fabric or a laundry washing machine with at least one strain of *Bacillus* capable of inhibiting or preventing the production of malodor caused by *Enterobacter* sp. wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

41. A method of inhibiting or preventing the production of laundry malodor caused by *Cronobacter sakazakii* comprising contacting a fabric or a laundry washing machine with at least one strain of *Bacillus* capable of inhibiting or preventing the production of malodor caused by *Cronobacter sakazakii* wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus*

*amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

42. A method of inhibiting or preventing the production of laundry malodor caused by *Bacillus megaterium* comprising contacting a fabric or a laundry washing machine with at least one strain of *Bacillus* capable of inhibiting or preventing the production of malodor caused by *Bacillus megaterium* wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

43. A method of inhibiting or preventing the production of laundry malodor caused by *Sphingobacterium faecium* comprising contacting a fabric or a laundry washing machine with at least one strain of *Bacillus* capable of inhibiting or preventing the production of malodor caused by *Sphingobacterium faecium* wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

44. A method of inhibiting or preventing the production of laundry malodor caused by *Enterobacter cloacae* comprising contacting a fabric or a laundry washing machine with at least one strain of *Bacillus* capable of inhibiting or preventing the production of malodor caused by *Enterobacter cloacae* wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

45. A method of inhibiting or preventing the production of laundry malodor caused by *Pseudomonas veronii* comprising contacting a fabric or a laundry washing machine with at least one strain of *Bacillus* capable of inhibiting or preventing the production of malodor caused by *Pseudomonas veronii* wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

46. A method of inhibiting or preventing the production of laundry malodor caused by *Microbacterium luteolum* comprising contacting a fabric or a laundry washing machine with at least one strain of *Bacillus* capable of inhibiting or preventing the production of malodor caused by *Microbacterium luteolum* wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

47. A method of inhibiting or preventing the production of laundry malodor caused by *Morganella morganii* comprising contacting a fabric or a laundry washing machine with at least one strain of *Bacillus* capable of inhibiting or preventing the production of malodor caused by *Morganella morganii* wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

48. A method of inhibiting or preventing the production of laundry malodor caused by *Bacillus cereus* comprising contacting a fabric or a laundry washing machine with at least one strain of *Bacillus* capable of inhibiting or preventing the production of malodor caused by *Bacillus cereus* wherein the at least one strain of is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

49. A method of inhibiting or preventing the production of laundry malodor caused by *Pseudomonas* sp. comprising contacting a fabric or a laundry washing machine with at least one strain of *Bacillus* capable of inhibiting or preventing the production of malodor caused by *Pseudomonas* sp. wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

50. A method of inhibiting or preventing the production of laundry malodor caused by *Pseudomonas-marginalis* comprising contacting a fabric or a laundry washing machine with at least one strain of *Bacillus* capable of inhibiting or preventing the production of malodor caused by *Pseudomonas-marginalis* wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

51. A method of inhibiting or preventing the production of laundry malodor caused by *Citrobacter* sp. comprising contacting a fabric or a laundry washing machine with at least one strain of *Bacillus* capable of inhibiting or preventing the production of malodor caused by *Citrobacter* sp. wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

52. A method of inhibiting or preventing the production of laundry malodor caused by *Escherichia coli* strain JCLys5 comprising contacting a fabric or a laundry washing machine with at least one strain of *Bacillus* capable of inhibiting or preventing the production of malodor caused by *Escherichia coli* strain JCLys5 wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

53. A method of inhibiting or preventing the production of laundry malodor caused by *Roseomonas aquatic* comprising contacting a fabric or a laundry washing machine with at least one strain of *Bacillus* capable of inhibiting or preventing the production of malodor caused by *Roseomonas aquatic* wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

54. A method of inhibiting or preventing the production of laundry malodor caused by *Pseudomonas panipatensis* comprising contacting a fabric or a laundry washing machine with at least one strain of *Bacillus* capable of inhibiting or preventing the production of malodor caused by *Pseudomonas panipatensis* wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

55. A method of inhibiting or preventing the production of laundry malodor caused by *Brevibacillus subtilis subtilis* comprising contacting a fabric or a laundry washing machine with at least one strain of *Bacillus* capable of inhibiting or preventing the production of malodor caused by *Brevibacillus subtilis subtilis* wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

56. A method of inhibiting or preventing the production of laundry malodor caused by *Micrococcus luteus* comprising contacting a fabric or a laundry washing machine with at least one strain of *Bacillus* capable of inhibiting or preventing the production of malodor caused by *Micrococcus luteus* wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

57. A method of inhibiting or preventing the production of laundry malodor caused by *Bacillus pumilus* comprising contacting a fabric or a laundry washing machine with at least one strain of *Bacillus* capable of inhibiting or preventing the production of malodor caused by *Bacillus pumilus* wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

58. A method of inhibiting or preventing the production of laundry malodor caused by *Ralstonia eutropha* comprising contacting a fabric or a laundry washing machine with at least one strain of *Bacillus* capable of inhibiting or preventing the production of malodor caused by *Ralstonia eutropha* wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

59. A method of inhibiting or preventing the production of laundry malodor caused by *Caulobacter fusiformis* comprising contacting a fabric or a laundry washing machine with at least one strain of *Bacillus* capable of inhibiting or preventing the production of malodor caused by *Caulobacter fusiformis* wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

60. A method of inhibiting or preventing the production of laundry malodor caused by *Stenotrophomonas maltophilia* comprising contacting a fabric or a laundry washing machine with at least one strain of *Bacillus* capable of inhibiting or preventing or prevent the production of malodor caused by *Stenotrophomonas maltophilia* wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

61. A method of inhibiting or preventing the production of laundry malodor caused by *Rhodococcus opacus* comprising contacting a fabric or a laundry washing machine with at least one strain of *Bacillus* capable of inhibiting or preventing the production of malodor caused by *Rhodococcus*

*opacus* wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

62. A method of inhibiting or preventing the production of laundry malodor caused by *Breviundimonas intermedia* comprising contacting a fabric or a laundry washing machine with at least one strain of *Bacillus* capable of inhibiting or preventing the production of malodor caused by *Breviundimonas intermedia* wherein the at least one strain of is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

63. A method of inhibiting or preventing the production of laundry malodor caused by *Agrobacterium tumefaciens* comprising contacting a fabric or a laundry washing machine with at least one strain of *Bacillus* capable of inhibiting or preventing the production of malodor caused by *Agrobacterium tumefaciens* wherein the at least one strain of *Bacillus* is selected from the group consisting of *Bacillus pumilus* strain NRRL B-50016; *Bacillus amyloliquefaciens* strain NRRL B-50017; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; and combinations thereof.

64. A composition adapted for application to the interior of a washing machine comprising a carrier and at least one microorganism.

65. The composition of paragraph 64, wherein the at least one microorganism is at least one species of *Bacillus*.

66. The composition of paragraph 65, wherein the at least one species of *Bacillus* is selected from the group consisting of *Bacillus subtilis, Bacillus amyloliquefaciens, Bacillus pumilus, Bacillus licheniformis, Bacillus atrophaeus* and combinations thereof.

67. The composition of paragraph 65 or 66, wherein the at least one species of *Bacillus* is selected from the group consisting of *Bacillus pumilus* strain NRRL B-50016; *Bacillus amyloliquefaciens* strain PTA-7792; *Bacillus amyloliquefaciens* strain PTA-7543; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus subtilis* strain PTA-7547; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; *Bacillus amyloliquefaciens* strain NRRL B-50706; and combinations thereof.

68. The composition of any of paragraphs 64-67, wherein the composition is a solid, semi-solid, gel, liquid, aerosol, emulsion, or powder.

69. The composition of any of paragraphs 64-68, which further comprises a surfactant 70. The composition of any of paragraphs 64-69, which further comprises one or more enzymes.

71. The composition of any of paragraphs 64-70, wherein the enzyme is selected from the group consisting of proteases, alpha-amylases, cellulases, lipases, peroxidases/oxidases, pectate lyases, and mannanases, or mixtures thereof.

72. The composition of any of paragraphs 64-71, which further comprises one or more ingredients selected from the group consisting of dispersants, stabilizers, anti-microbial agents, fragrances, dyes, and biocides.

73. The composition of any of paragraphs 64-72, wherein the composition is solid, semi-solid, gel, liquid, aerosol, emulsion, or powder composition adapted for application as a detergent, fabric softener, or any other laundry additive.

74. The composition of any of paragraphs 64-73, wherein the least one microorganism is capable of inhibiting or preventing the production of malodor caused by at least one malodor causing bacteria or at least one bacteria capable of causing malodor.

75. A composition adapted for application to a fabric comprising a carrier containing at least one microorganism.

76. The composition of paragraph 75, wherein the at least one microorganism is at least one species of *Bacillus* or a substance derived therefrom.

77. The composition of paragraph 76, wherein the at least one species of *Bacillus* is selected from the group consisting of *Bacillus subtilis, Bacillus amyloliquefaciens, Bacillus pumilus, Bacillus licheniformis, Bacillus atrophaeus,* and combinations thereof.

78. The composition of paragraph 76 or 77, wherein the at least one species of *Bacillus* is selected from the group consisting of *Bacillus pumilus* strain NRRL B-50016; *Bacillus amyloliquefaciens* strain NRRL B-50017, *Bacillus amyloliquefaciens* strain PTA-7792; *Bacillus amyloliquefaciens* strain PTA-7543; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus subtilis* strain PTA-7547; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus*

*amyloliquefaciens* strain NRRL B-50399; *Bacillus licheniformis* strain NRRL B-50014; *Bacillus licheniformis* strain NRRL B-50015 *Bacillus amyloliquefaciens* strain NRRL B-50706; and combinations thereof.

79. The composition of any of paragraphs 75-78, wherein the composition is a solid, semi-solid, gel, liquid, aerosol, emulsion, or powder.

80. The composition of any of paragraphs 75-79, which further comprises a surfactant 81. The composition of any of paragraphs 75-80, which further comprises one or more enzymes.

82. The composition of any of paragraphs 75-81, wherein the enzyme is selected from the group consisting of proteases, alpha-amylases, cellulases, lipases, peroxidases/oxidases, pectate lyases, and mannanases, or mixtures thereof.

83. The composition of any of paragraphs 75-82 which further comprises one or more ingredients selected from the group consisting of dispersants, stabilizers, anti-microbial agents, fragrances, dyes, and biocides.

84. The composition of any of paragraphs 75-83, wherein the composition is solid, liquid, aerosol, or powder composition adapted for application as a detergent, fabric softener, or any other laundry additive.

85. The composition of paragraph 75, wherein the least one microorganism is capable of inhibiting or preventing the production of malodor caused by at least one malodor causing bacteria or at least one bacteria capable of causing malodor.

86. A method of inhibiting or preventing the production of laundry malodor caused by bacteria capable of producing odiferous compounds comprising subjecting the odiferous compounds to at least one microorganism capable of using the odiferous compound as a food source.

87. The method of paragraph 86, wherein the at least one microorganism is at least one species of *Bacillus*.

88. The method of paragraph 87, wherein the at least one species of *Bacillus* is selected from the group consisting of *Bacillus subtilis, Bacillus amyloliquefaciens, Bacillus pumilus, Bacillus licheniformis, Bacillus atrophaeus*; and combinations thereof.

89. The method of any of paragraphs 86-88, wherein the at least one species of *Bacillus* is selected from the group consisting of *Bacillus pumilus* strain NRRL B-50016; *Bacillus amyloliquefaciens* strain NRRL B-50017, *Bacillus amyloliquefaciens* strain PTA-7792; *Bacillus amyloliquefaciens* strain PTA-7543; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus subtilis* strain PTA-7547; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; *Bacillus amyloliquefaciens* strain NRRL B-50706; and combinations thereof.

90. The method of any of paragraphs 86-89, wherein the bacteria capable of producing the odiferous compound is at least one bacterial species selected from the group consisting of *Bacillus amyloliquefaciens, Acinetobacter junii, Bacillus subtilis, Janibacter melois, Sphingobium ummariense, Sphingomonas panni,* Sphingomonadaceae sp., *Actinobacter tandoii, Junibacter melonis, Curtobacterium flaccumfaciens, Flavobacterium denitrificans, Staphylococcus epidermidis, Escherichia coli, Leclercia adecarboxylata, Enterobacter* sp.*, Cronobacter sakazakii, Bacillus megaterium, Sphingobacterium faecium, Enterobacter cloacae, Pseudomonas veronii, Microbacterium luteolum, Morganella morganii, Bacillus cereus, Pseudomonas* sp.*, Pseudomonas-marginalis, Citrobacter* sp.*, Escherichia coli* strain JCLys5*, Roseomonas aquatic, Pseudomonas panipatensis, Brevibacillus subtilis subtilis, Micrococcus luteus, Bacillus pumilus, Ralstonia eutropha, Caulobacter fusiformis, Stenotrophomonas maltophilia, Rhodococcus opacus, Breviundimonas intermedia, Agrobacterium tumefaciens*, and combinations thereof.

91. The method of any of paragraphs 84-88, wherein the odiferous compound is at least one compound selected from the group consisting of guaiacol, ethyl butyrate, cis-4-heptenal, 4-methyloctanoic acid, p-anisaldehyde, isovaleric acid, and combinations thereof.

92. A method of inhibiting or preventing the production of malodor caused by at least one malodor causing microorganism or at least one microorganism capable of causing malodor, comprising contacting a fabric or a washing machine with at least one non-odor causing microorganism capable of inhibiting or preventing the production of malodor caused by the at least one malodor causing microorganism or the at least one microorganism capable of causing malodor.

93. The method of paragraph 92, wherein the method comprises contacting the at least one malodor causing microorganism or the at least one microorganism capable of causing malodor capable of causing laundry malodor.

94. The method of paragraph 92 or 93, wherein the method comprises contacting an odor generating compound derived from the at least one malodor causing microorganism or the at least one microorganism capable of causing malodor capable of causing laundry malodor.

95. The method of paragraph 92 or 93, wherein the contacting comprises administering the at least one non-odor causing microorganism to a laundry washing machine.

96. The method of any of paragraphs 92-95, wherein the contacting is done during a washing process.

97. The method of any of paragraphs 92-96, wherein the contacting is done to a new washing machine.

98. The method of any of paragraphs 92-96, wherein the contacting is done to a washing machine following one or more uses of said washing machine.

99. The method of any of paragraphs 92-98, wherein the at least one non-odor causing microorganism is at least one species of *Bacillus*.

100. The method of paragraph 99, wherein the at least one species of *Bacillus* is selected from the group consisting of *Bacillus subtilis, Bacillus amyloliquefaciens, Bacillus pumilus, Bacillus licheniformis, Bacillus atrophaeus*, and combinations thereof.

101. The method of paragraph 99 or 100, wherein the at least one species of *Bacillus* is selected from the group consisting of *Bacillus pumilus* strain NRRL B-50016; *Bacillus amyloliquefaciens* strain NRRL B-50017, *Bacillus amyloliquefaciens* strain PTA-7792; *Bacillus amyloliquefaciens* strain PTA-7543; *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus subtilis* strain PTA-7547; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136; *Bacillus* amyloliquefaciens strain NRRL B-50141; *Bacillus amyloliquefaciens* strain NRRL B-50399; *Bacillus licheniformis* strain NRRL B-50014; *Bacillus licheniformis* strain NRRL B-50015; *Bacillus amyloliquefaciens* strain NRRL B-50706; and combinations thereof.

102. The method of any of paragraphs 92-101, wherein the at least one malodor causing microorganism or the at least one microorganism capable of causing malodor is at least one bacterial species selected from the group consisting of *Bacillus amyloliquefaciens, Acinetobacter junii, Bacillus subtilis, Janibacter melois, Sphingobium ummariense, Sphingomonas panni,* Sphingomonadaceae sp., *Actinobacter tandoii, Junibacter melonis, Curtobacterium flaccumfaciens, Flavobacterium denitrificans, Staphylococcus epidermidis, Escherichia coli, Leclercia adecarboxylata, Enterobacter* sp., *Cronobacter sakazakii, Bacillus megaterium, Sphingobacterium faecium, Enterobacter cloacae, Pseudomonas veronii, Microbacterium luteolum, Morganella morganii, Bacillus cereus, Pseudomonas* sp., *Pseudomonas-marginalis, Citrobacter* sp., *Escherichia coli* strain JCLys5, *Roseomonas aquatic, Pseudomonas panipatensis, Brevibacillus subtilis subtilis, Micrococcus luteus, Bacillus pumilus, Ralstonia eutropha, Caulobacter fusiformis, Stenotrophomonas maltophilia, Rhodococcus opacus, Breviundimonas intermedia, Agrobacterium tumefaciens,* and combinations thereof.

The following examples are included for illustrative purposes only and are not intended to limit the scope of the invention.

EXAMPLES

Example 1: Isolation of Organisms Growing in Fouled Household Washing Machines

Household washing machines known to have malodor problems were swabbed for bacterial or fungal populations. The swabs were processed by submerging the swab in Phosphate Buffer (Weber Scientific Cat #3127-29) and spreading dilutions onto Standards Methods and Potato Dextrose agars (Smith River Biologicals Cat #11-00450 and 11-00740C) with overnight incubations at 21° C. After successive transfers to obtain purity, ~113 bacterial/fungal isolates were obtained. Twenty-nine of these isolates were identified by 16s rDNA, 500 bp analysis using Applied Biosystems 3130 Genetic Analyzer Instrument and Geneious Pro 4.7.5 phylogenetics analysis or contracted through Midi Labs (Newark, Del.). The following isolates were obtained and listed in Table 1.

TABLE 1

Strains of Odorigenic Microbes Isolated from a Household Washing Machine
Identification of Strain

*Bacillus subtilis*
*Bacillus subtilis*
*Bacillus subtilis*
*Bacillus amyloliquifaciens*
*Bacillus amyloliquifaciens*
*Bacillus amyloliquifaciens*
*Bacillus amyloliquifaciens*
*Bacillus amyloliquifaciens*
*Bacillus amyloliquifaciens*
*Sphingobium ummariense*
Unknown Sphingomonadaceae
*Sphingomonas panni*
*Sphingomonas ursinicola*

TABLE 1-continued

Strains of Odorigenic Microbes Isolated from a Household Washing Machine
Identification of Strain

*Acinetobacter tandoii*
*Acinetobacter junii*
*Curtobacterium flaccumfaciens*
*Janibacter melonis*
Unknown *Pseudomonas*
*Flavobacterium denitrificans*
*Micrococcus luteus*
*Bacillus pumilus*
*Ralstonia eutropha*
*Caulobacter fusiformis*
*Stenotrophomonas maltophilia*
*Micrococcus luteus*
*Micrococcus luteus*
*Rhodococcus opacus*
*Breviundimonas intermedia*
*Agrobacterium tumefaciens*

Example 2: Isolation of Odorigenic Bacteria from Human Soiled Fabrics

Fifty-four volunteers from across 10 States in the USA donated t-shirts (100% cotton or 100% polyester) and socks after engaging in athletic activities. Swatches of soiled fabric (cut-out t-shirt armpits or socks) were incubated at 30° C. in sterile bottles for 7 days to allow development of malodor. A phosphate buffer (Weber Scientific Cat #3127-29) was added to the bottles containing the swatches and those bottles were placed into the tumble shaker and shaken for 30 minutes. The buffer was transferred to sterile 50 ml tubes and centrifuged for 10 minutes at 5,000 rpm. Supernatant from the centrifugation was discarded and the pellet was resuspended in 1 ml of phosphate buffer. Total bacterial counts were done by plating serial dilutions on Standard Methods agar plates (Smith River Biologicals, Ferrum, Va. Cat #11-00450). Plates were incubated at room temperature (approx. 26° C.). After 48 hrs, colonies were counted and those colonies having a different colony morphology were selected for and re-streaked in fresh medium. Pure cultures from individual isolates were evaluated for malodor production on Standard Methods agar plates by a sensory panel (7-10 panelists).

A total of 362 bacterial isolates were recovered from the textiles (T-shirts and socks) and 55 of these strains were evaluated by sensory panel as malodor producers. Twenty-five strains were ranked as the worst malodor producers and identified by 16s rDNA at MIDI Labs. The following isolates were obtained and listed in Table 2.

TABLE 2

List of odorigenic bacteria isolated from human soiled fabrics
Identification of Strain

*Escherichia coli*
*Leclercia adecarboxylata*
*Enterobacter* sp.
*Cronobacter sakazakii*
*Enterobacter* sp.
*Bacillus megaterium*
*Sphingobacterium faecium*
*Enterobacter cloacae*
*Pseudomonas veronii*
*Microbacterium luteolum*
*Morganella morganii*
*Morganella morganii*

TABLE 2-continued

List of odorigenic bacteria isolated
from human soiled fabrics
Identification of Strain Morganella morganii
Bacillus cereus
Pseudomonas sp.
Pseudomonas sp.
Pseudomonas-marginalis
Leclercia adecarboxylata
Citrobacter sp.
Escherichia coli strain JCLys5
Bacillus megaterium
Roseomonas aquatic
Pseudomonas panipatensis
Brevibacillus subtilis subtilis
Enterobacter sp.

Example 3: Zone of Inhibition Experiment

Odorigenic isolates (see Tables 1 and 2) were tested in a zone of inhibition Petri plate experiment against *Bacillus* spp. putative biocontrol (odor control) candidates as follows: *Bacillus* candidates (NRRL B-50136, NRRL B-50015, NRRL B-50016, NRRL B-50141, NRRL B-50018, PTA-7541, PTA-7792, PTA-7543, PTA-7544, PTA-7545, PTA-7546, PTA-7547, PTA-7549, PTA-7793, PTA-7790, PTA-7791, NRRL B-50706, and NRRL B-50399) were grown separately in Plate Count broth (Difco DF0751-17-2, made according to manufacturer's instructions) for 18 to 24 hours resulting in appx $10^7$ to $10^8$ cfu/ml culture. Odorigenic isolates from Tables 1 and 2 were grown individually for 18 to 24 hours (appx $10^8$ to $10^{10}$ culture) in Plate Count broth and then streaked to form a lawn on the surface of Standard Methods agar plates (Smith River Biologicals, Ferrum, Va.) Four 5 mm holes were bored into the agar with a sterile stainless steel tube. 50 µl of each *Bacillus* liquid culture were delivered into the holes (1 strain per hole) and the plate was incubated for 18 to 48 hours at 35° C., agar side down. Inhibited odorigenic isolate lawn in proximity to a hole was scored as positive biocontrol by the *Bacillus* candidate. The zone of inhibition was also measured in millimeters (mm) to allow semi-quantitative assessment of control.

The plates were then examined for Zones of Clearing/Inhibition. If there was no observable zone around the well, then a blank was recorded. If there was an outgrowth of the test strains, a zone of inhibition could not be determined and an "OG" was recorded. If there was a zone around the well, the diameter of the zone was recorded. "ND" means not determined.

Results are recorded in Tables 3A, 3B, 3C and 3D wherein "OG" indicates out growth for the test strains. If ZOI could not be determined and a blank entry indicates negative ZOI results.

While results can be difficult to repeat with numerical exactitude, general trends may still be observed. All conditions should be substantially identical in order to obtain similar results including: similar starting count for both undesirable strains and *Bacillus* strains, incubation times need to be similar to ensure proper cell growth and/or metabolite production, dosing and incubation times need to be nearly identical as a few hours can make a large difference.

TABLE 3A

Results of Petri Plate Inhibition Assays of Washing Machine Isolates

| ODORIGENIC | TEST STRAINS | | | | | | | | |
|---|---|---|---|---|---|---|---|---|---|
| | NRRL B-50136 | NRRL B-50014 | NRRL B-50015 | NRRL B-50016 | NRRL B-50141 | NRRL B-50018 | PTA-7541 | PTA-7792 | PTA-7543 |
| B. AMYLOLIQUEFACIENS | 15.47 | | | | | | 10.26 | | 9.62 |
| ACINETOBACTER JUNII | | | | | | OG | OG | OG | OG |
| B. SUBTILIS | | | | | | | | | |
| JANIBACTER MELONIS | 22.93 | 12.58 | | 17.23 | 18.54 | OG | OG | OG | OG |
| SPHINGOBIUM UMMARIENSE | | | | 13.82 | | 17.88 | 17.08 | | |
| B. SUBTILIS | | | | | | | | | |
| SPHINGOMONAS PANNI | | | | | 14.15 | OG | OG | OG | OG |
| SPHINGOMONADACEAE | OG | | | OG | 14.23 | 19.1 | 21.66 | OG | OG |
| ACUNETOBACTER TANDOII | OG | | | | OG | OG | OG | OG | OG |
| JANIBACTER MELONIS | 17.18 | | | | | | 10.48 | | 10.74 |
| B. AMYLOLIQUEFACIENS | 14.92 | | | | | | | | |
| B. AMYLOLIQUEFACIENS | 16.17 | | | | | | | | |
| CURTOBACTERIUM FLACCUMFACIENS | 9.44 | | | 14.96 | | OG | 12.06 | OG | OG |
| B. SUBTILIS | 10.69 | | | | | | | | 12 |
| B. AMYLOLIQUEFACIENS | 16.88 | | | | | | | | |
| FLAVOBACTERIUM DENITRIFICANS | 9.42 | | | | | OG | OG | OG | OG |
| B. AMYLOLIQUEFACIENS | 8.63 | | | | | | | | |
| STAPHYLOCOCCUS EPIDERMIDIS | 25.48 | 9.95 | | 21.04 | 10.15 | 27.9 | 23.01 | | |
| RHODOCOCCUS OPACUS | 8.875 | | 9.555 | 12.16 | 15.865 | ND | 12.37 | 13.805 | 15.59 |
| BACILLUS PUMILUS | 13.25 | 8.07 | 7.71 | | 14.09 | ND | 15.09 | 16.07 | 16.865 |
| AGROBACTERIUM TUMEFACIENS | | | | | 13.56 | ND | 14.055 | 15.65 | 14.495 |
| ML5-2 | | | | 12.23 | 17.255 | ND | 19.73 | 19.185 | 18.295 |
| BREVUNDIMONAS INTERMEDIA | 9.69 | 14.965 | 9.655 | 15.18 | 22.245 | ND | 21.88 | 21.77 | 21.24 |

TABLE 3A-continued

Results of Petri Plate Inhibition Assays of Washing Machine Isolates

| ODORIGENIC | NRRL B-50136 | NRRL B-50014 | NRRL B-50015 | NRRL B-50016 | NRRL B-50141 | NRRL B-50018 | PTA-7541 | PTA-7792 | PTA-7543 |
|---|---|---|---|---|---|---|---|---|---|
| MICROCOCCUS LUTEUS | 14.255 | 11.285 | 12.185 | 14.73 | 20.24 | ND | 21.275 | 20.305 | 22.26 |
| MICROCOCCUS LUTEUS | 22.49 | 17.61 | 18 | 27.82 | 28.005 | ND | 27.61 | 27.2 | 29.445 |
| MICROCOCCUS LUTEUS | 15.04 | 11.11 | 10.1 | 14.885 | 23.1 | ND | 21.15 | 22.1 | 22.255 |
| RALSTONIA EUTROPHA | | | | | | ND | | | |
| CAULIBACTER FUSIFORMIS | 10.545 | 8.82 | | 16.15 | 21.555 | ND | 20.405 | 21.395 | 22.76 |

TABLE 3B

Results of Petri Plate Inhibition Assays of Washing Machine Isolates

| ODORIGENIC | PTA-7544 | PTA-7545 | PTA-7546 | PTA-7547 | PTA-7549 | PTA-7793 | PTA-7790 | PTA-7791 | NRRL B-50399 | NRRL B-50706 |
|---|---|---|---|---|---|---|---|---|---|---|
| B. AMYLOLIQUEFACIENS | | | 10.57 | | | | | | | ND |
| ACINETOBACTER JUNII | OG | OG | OG | OG | 10.4 | OG | OG | OG | 13.03 | ND |
| B. SUBTILIS | | | | | | | | | | ND |
| JANIBACTER MELONIS | OG | OG | OG | OG | OG | OG | OG | OG | OG | ND |
| SPHINGOBIUM UMMARIENSE | | | | | 19.57 | | | | | ND |
| B. SUBTILIS | 13.36 | 13.74 | 12.47 | | 11.24 | 18.26 | 10.5 | | | ND |
| SPHINGOMONAS PANNI | OG | OG | OG | OG | OG | OG | OG | OG | OG | ND |
| SPHINGOMONADACEAE | 20.39 | OG | OG | OG | OG | OG | OG | OG | OG | ND |
| ACUNETOBACTER TANDOII | OG | OG | OG | OG | 9.3 | OG | OG | OG | OG | ND |
| JANIBACTER MELONIS | | 9.06 | 9.32 | 10.59 | | 9.79 | | 11.28 | | ND |
| B. AMYLOLIQUEFACIENS | | | | | | | | 11.16 | | ND |
| B. AMYLOLIQUEFACIENS | | | 6.91 | | | | OG | OG | OG | ND |
| CURTOBACTERIUM FLACCUMFACIENS | OG | OG | OG | 14.96 | OG | OG | OG | OG | OG | ND |
| B. SUBTILIS | | 11.94 | 10.48 | | 11.92 | 12.75 | | 21.25 | 13.82 | ND |
| B. AMYLOLIQUEFACIENS | | | | | | | | 15.3 | 15.88 | ND |
| FLAVOBACTERIUM DENITRIFICANS | OG | OG | OG | OG | OG | OG | OG | OG | OG | ND |
| B. AMYLOLIQUEFACIENS | | | | | | | | | | ND |
| STAPHYLOCOCCUS EPIDERMIDIS | 29.77 | 30.87 | 30.69 | | 26.46 | 29.18 | 28.5 | 29.63 | 31.94 | ND |
| RHODOCOCCUS OPACUS | 7.165 | 14.13 | 15.465 | 15.425 | 17.31 | 14.165 | 13.295 | 13.925 | 8.51 | 15.415 |
| BACILLUS PUMILUS | 15.8 | 13.175 | 15.09 | 8.51 | 15.46 | 15.77 | 15.6 | 12.665 | 16.035 | 16.34 |
| AGROBACTERIUM TUMEFACIENS | 12.23 | 15.73 | | | 13.98 | 14.29 | 15.38 | 14.31 | 16.735 | 15.995 |
| ML5-2 | 17.045 | 21.21 | 14.58 | 9.855 | 18.42 | 19.02 | 20.185 | 18.3 | 19.225 | 19.245 |
| BREVUNDIMONAS INTERMEDIA | 20.71 | 22.39 | 17.445 | 9.3 | 22.18 | 21.2 | 21.225 | 21.785 | 21.695 | 22.395 |
| MICROCOCCUS LUTEUS | 20.765 | 20.01 | 19.62 | 18.7 | 21.425 | 19.19 | 21.165 | 20.82 | 19.1 | 20.72 |
| MICROCOCCUS LUTEUS | 27.535 | 26.575 | 26.635 | 24.135 | 26.79 | 24.655 | 27.59 | 26.865 | 25.39 | 27.845 |
| MICROCOCCUS LUTEUS | 22.19 | 21.805 | 20.405 | 20.31 | 22.31 | 21.035 | 23.55 | 23.405 | 20.825 | 21.65 |
| RALSTONIA EUTROPHA | | | | | | | | | | |
| CAULIBACTER FUSIFORMIS | 21.605 | 21.435 | 18.35 | 8.67 | 20.14 | 19.175 | 22.45 | 22.13 | 20.5 | 20.335 |

TABLE 3C

Results of Petri Plate Inhibition Assays of Textile Isolates

| ODORIGENIC | TEST STRAINS | | | | | | | | |
|---|---|---|---|---|---|---|---|---|---|
| | NRRL B-50136 | NRRL B-50014 | NRRL B-50015 | NRRL B-50016 | NRRL B-50141 | NRRL B-50018 | PTA-7541 | PTA-7792 | PTA-7543 |
| *BACILLUS CEREUS* | 9.33 | | | 8.2 | 11.525 | ND | 13.08 | 12.325 | 11.23 |
| *PSEUDOMONAS* SP. | 11.745 | | | 11.375 | 9.06 | ND | 9.525 | 9.52 | 9.4 |
| *ENTEROBACTER CLOACAE* | | | | | 28.44 | ND | 25.845 | 24.975 | 27.865 |
| *CITROBACTER* SP. | | | | | 11.47 | ND | 11.17 | 11.205 | |
| *BACILLUS MEGATERIUM* | 10.505 | 9.81 | 10.17 | 15.615 | 24.565 | ND | 24.665 | 24.875 | 26.245 |
| *ENTEROBACTER* SP. | | | | | 0 | ND | 8.595 | 9.46 | 9.23 |
| *LECLERCIA ADECARBOXYLATA* | | | | | 13.365 | ND | 12.735 | 13.825 | 13.4 |
| *LECLERCIA ADECARBOXYLATA* | | | | | 8.76 | ND | 9.135 | 10.785 | 10.175 |
| *PSEUDOMONAS* SP. | 14.265 | | | | 12.55 | ND | | | |
| *E. COLI* | | | | | 8.83 | ND | 9.42 | 9.75 | 9.4 |
| *PSEUDOMONAS VERONII* | | | | | 7.36 | ND | | | |
| *MICROBACTERIUM LUTEOLUM* | | 8.51 | 8.01 | | 7.46 | ND | 7.925 | | |
| *MORGANELLA MORGANII* | | | | | 11.255 | ND | 10.69 | 12.83 | 12.41 |
| *SPHINGOBACTERIUM FAECIUM* | | | | 13.485 | 19.69 | ND | 19.26 | 20.48 | 20.62 |
| *ENTEROBACTER* SP. | | | | 9.625 | 11.245 | ND | 10.585 | 12.335 | 12.755 |
| *ROSEOMONAS AQUATIC* | | | | 11.395 | 12.53 | ND | 13.66 | 16.47 | 12.86 |
| *E. COLI* STRAIN JCLYS5 | | | | | 9.975 | ND | 10.63 | 10.75 | 12.055 |
| *PSEUDOMONAS MARGINALIS* | | | | | 8.75 | ND | 8.925 | 9.99 | 8.93 |
| *MORGANELLA MORGANII* | | | | | 9.03 | | 9.605 | 11.12 | 9.89 |
| *BREVIBACILLUS SUBTILIS SUBTILIS* | 10.56 | | | | | | ND | | |
| *CRONOBACTER SAKAZAKII* | | | | 4.595 | | ND | 9.53 | 11.75 | 10.85 |
| *ENTEROBACTER* SP. | | | | 8.845 | 11.87 | ND | 12.5 | 11.88 | 11.695 |
| *MORGANELLA MORGANII* | | | | | 9.59 | ND | 9.845 | 5.825 | |
| *BACILLUS MEGATERIUM* | 13.475 | 9.245 | 8.715 | 11.61 | 21.65 | ND | 20.63 | 23.625 | 18.37 |
| *PSEUDOMONAS PANIPATENSIS* | 5.18 | 8.425 | | 13.725 | 15.3 | ND | 11.125 | | |

TABLE 3D

Results of Petri Plate Inhibition Assays of Textile Isolates

| ODORIGENIC | TEST STRAINS | | | | | | | | | |
|---|---|---|---|---|---|---|---|---|---|---|
| | PTA-7544 | PTA-7545 | PTA-7546 | PTA-7547 | PTA-7549 | PTA-7793 | PTA-7790 | PTA-7791 | NRRL B-50399 | NRRL B-50706 |
| *BACILLUS CEREUS* | 12.52 | 12.67 | 11.115 | 8.225 | 11.77 | 12.495 | 11.78 | 12.6 | 11.205 | 12.72 |
| *PSEUDOMONAS* SP. | 8.49 | 10.215 | 8.91 | | 11.615 | 8.59 | 9.33 | 8.435 | 10.275 | 9.945 |
| *ENTEROBACTER CLOACAE* | 27.71 | 26.6 | 27.83 | 25.49 | 20.925 | 23.99 | 22.75 | 24.13 | 27.395 | 9.66 |
| *CITROBACTER* SP. | 12.18 | 11.98 | | | 11.145 | 11.635 | 10.32 | 10.405 | 10.545 | 12.58 |
| *BACILLUS MEGATERIUM* | 21.4 | 25.615 | 24.155 | 12.615 | 23.875 | 24.915 | 25.915 | 22.075 | 26.075 | 26.235 |
| *ENTEROBACTER* SP. | 9.065 | 9.235 | | 11.69 | | 10.025 | 9.21 | 9.43 | 9.635 | 8.995 |
| *LECLERCIA ADECARBOXYLATA* | 13.515 | 13.775 | 10.64 | 12.875 | 13.335 | 11.805 | 12.175 | 12.15 | 13.71 | 14.405 |
| *LECLERCIA ADECARBOXYLATA* | 7.915 | 12.16 | | 8.44 | 9.97 | 10.145 | 11.055 | 8.345 | 10.495 | 11.425 |
| *PSEUDOMONAS* SP. | | | | | | 15.125 | | | | 14.9 |
| *E. COLI* | 9.825 | 9.89 | | | 9.445 | 9.63 | 9.515 | 9.29 | 9.21 | 11.04 |
| *PSEUDOMONAS VERONII* | | | | | | | | | | 8.01 |

TABLE 3D-continued

Results of Petri Plate Inhibition Assays of Textile Isolates

| | TEST STRAINS | | | | | | | | | |
|---|---|---|---|---|---|---|---|---|---|---|
| ODORIGENIC | PTA-7544 | PTA-7545 | PTA-7546 | PTA-7547 | PTA-7549 | PTA-7793 | PTA-7790 | PTA-7791 | NRRL B-50399 | NRRL B-50706 |
| MICROBACTERIUM LUTEOLUM | | | | 8.2 | | | 8.305 | | | |
| MORGANELLA MORGANII | 11.685 | 12.345 | 9.535 | | 11.38 | 9.975 | 11.95 | 12.69 | 11.46 | 10.27 |
| SPHINGOBACTERIUM FAECIUM | 18.97 | 19.335 | 17.495 | 12.42 | 18.62 | 17.91 | 19.84 | 21.58 | 18.78 | 18.515 |
| ENTEROBACTER SP. | 12.59 | 11.485 | 9.705 | 9.02 | 11.43 | 10.785 | 11.25 | 12.18 | 9.79 | 10.985 |
| ROSEOMONAS AQUATIC | 13.885 | 18.35 | 15.29 | 10.02 | 16.35 | 16.995 | 17.465 | 13.975 | 18.575 | 16.16 |
| E. COLI STRAIN JCLYS5 | 11.435 | 10.91 | 9.935 | 8.96 | 11.785 | 11.545 | 12.04 | 10.36 | 11.515 | 9.59 |
| PSEUDOMONAS MARGINALIS | | | | | 8.555 | 8.175 | 10.13 | 8.84 | | 9.025 |
| MORGANELLA MORGANII | 9.96 | 10.6 | 9.105 | | 10.635 | 10.9 | 12.29 | 10.425 | 11.81 | |
| BREVIBACILLUS SUBTILIS SUBTILIS | | | | | | | 8.4 | | | |
| CRONOBACTER SAKAZAKII | 11.495 | 11.88 | 8.39 | | 10.38 | 11.275 | 10.835 | 10.065 | 12.99 | |
| ENTEROBACTER SP. | 10.22 | 11.095 | 10.9 | 9.92 | 12.39 | 11.23 | 10.885 | 9.89 | 10.875 | 11.87 |
| MORGANELLA MORGANII | | 9.255 | 9.32 | | 9.815 | 9.99 | 10.835 | 9.21 | 9.765 | 8.505 |
| BACILLUS MEGATERIUM | 21.525 | 21.99 | 20.56 | 11.815 | 21.385 | 20.525 | 20.73 | 19.62 | 21.16 | 21.85 |
| PSEUDOMONAS PANIPATENSIS | 10.61 | | 14.45 | 9.905 | 13.84 | 12.95 | 11.575 | 11.125 | 14.32 | 13.375 |

As reflected by tables 3A, 3B, 3C, and 3D, respectively, candidate test strains with the potential to inhibit laundry malodor could be pre-screened by ZOI assays against isolated odorigenic species.

Example 4—Biodegradation of Laundry Malodor Molecules by Beneficial Bacteria A sole carbon source utilization study was performed to determine whether strains NRRL B-50136, NRRL B-50014, NRRL B-50015, NRRL B-50016, NRRL B-50141, NRRL B-50018. PTA-7541, PTA-7792, PTA-7543, PTA-7544, PTA-7545, PTA-7546, PTA-7547, PTA-7549, PTA-7793, PTA-7790, PTA-7791, and NRRL B-50399 could grow on or biodegrade odorous compounds known to cause malodor in laundry (Munk, Signe et al., Microbial Survival and Odor in Laundry, *Journal of Surfactants and Detergents*. 4:4 (2001).

The 6 compounds, guaiacol (Sigma Cat # W253200-Sample-K), ethyl butyrate (Sigma Cat # W242705-Sample-K), cis-4-heptenal (Sigma Cat # W328901-Sample-K), 4-methyloctanoic acid (Sigma Cat # W357502-Sample-K), p-anisaldehyde (Sigma Cat # W267007-Sample), and isovaleric acid (Aldrich Cat #12,954-2) were diluted to 2000 ppm in water and one by one 20 µl was delivered to an individual well of a Becton Dickinson Oxygen Biosensor System microtiter plates (BD #353830). Minimal media (MM) was made as follows: $NH_4Cl$ (0.8 g/L), $MgSO_4$ (0.2 g/L), $CaCl_2.2H_2O$ (0.01 g/L), $Fe_2Na_2EDTA$ (0.015 g/L), $KH_2PO_4$ (3.06 g/L), MM Trace Minerals (1 ml). MM Trace Minerals was made as follows: $FeSO_4.7H_2O$ (28 mg/L), $ZnSO_4.7H_2O$ (140 mg/L), $MnSO4.H_2O$ (84 mg/L), $CoCl_2.6H_2O$ (24 mg/L), $CuSO4.6H_2O$ (25 mg/L), $NaMoO_4.2H_2O$ (24 mg/L). This minimal media was used as a diluent for the NZB *Bacillus* strains, adding 10 µl of a *Bacillus* culture grown 18-24 hrs in Difco Plate Count Broth to 170 ul of MM added to each microtiter well with odor compound. The microtiter plate was read in a Biotek FLx-8001 Fluorescent Plate Reader (Cat # FLx800-I) every 20 min for 99 hours with shaking at 10 sec intervals before every read, incubation at ambient temperature, and excitation/emission filters with specifications of 485/20 and 600/40, respectively. Fluorescence above background levels (ascertained from control wells with no odor molecule or carbon of any kind added) was deemed positive for growth and biodegradation on the odor molecule. NRRL B-50016, PTA-7546 and PTA-7790 did not utilize any of the odorous compounds. NRRL B-50015 did not grow. All compounds were utilized by at least 1 and at most 9 *Bacillus* strains while 4-methyloctanoic acid was utilized by the most. Results are recorded in Table 4.

TABLE 4

Results of Sole Carbon Source Utilization Study

| Test/Bacillus Strain(s) | Guaiacol | Ethyl-Butyrate | cis-4-Heptenal | 4-Methyloctanoic Acid | p-Anisaldehyde | Isovaleric Acid | # |
|---|---|---|---|---|---|---|---|
| NRRL B-50136 | + | − | − | − | − | − | 1 |
| NRRL B-50014 | − | − | + | − | − | − | 1 |
| NRRL B-50015 | DNG | DNG | DNG | DNG | DNG | DNG | 0 |
| NRRL B-50016 | − | − | − | − | − | − | 0 |
| NRRL B-50141 | − | − | + | − | − | − | 1 |
| NRRL B-50018 | + | − | + | − | − | − | 2 |
| PTA-7541 | + | + | − | + | − | − | 3 |
| PTA-7792 | + | − | + | − | + | − | 3 |
| PTA-7543 | + | − | − | + | − | − | 2 |
| PTA-7544 | − | − | + | − | − | − | 1 |
| PTA-7545 | − | − | − | + | − | + | 2 |
| PTA-7546 | − | − | − | − | − | − | 0 |
| PTA-7547 | − | + | + | + | − | − | 3 |
| PTA-7549 | − | − | − | + | − | + | 2 |
| PTA-7793 | + | − | + | + | − | − | 3 |
| PTA-7790 | − | − | − | − | − | − | 0 |
| PTA-7791 | − | − | + | + | − | − | 2 |
| NRRL B-50399 | − | − | + | − | − | − | 1 |
| # | 6 | 2 | 9 | 7 | 1 | 2 | |

Wherein "DNG" indicates the strain did not grow at the inoculum stage.

As reflected in Table 4, test strains were able to biodegrade the above referenced odoriferous compounds. Guaiacol was biodegraded by 6 test strains, ethyl butyrate was biodegraded by 2 test strains, cis 4-heptenal was biodegraded by 9 strains, 4-methyloctanoic acid was biodegraded by 7 strains, p-anisaldehyde was bio degraded by 1 strain, and isovaleric acid was degraded by 2 strains. Of the test strains subjected to the sole carbon source utilization study, 4 test strains were able to biodegrade 3 odiferous compounds, 5 test strains were able to biodegrade 2 odiferous compounds, 5 test strains were able to biodegrade a single odiferous compound, and 4 test strains were unable to biodegrade any of the odiferous compounds used in the study.

Example 5. Odor Mitigation on Post-Washed Textiles by Bacillus

Bacterial strains and culture conditions: Odor controlling Bacillus strains (NRRL B-50141, PTA-7543, PTA-7549) and the odorigenic strains (Cronobacter sakazakii; Pseudomonas veronii; Pseudomonas marginalis, and Microbacterium luteolum) (see Table 2) were isolated and maintained on Standard Methods agar plates (Smith River Biologicals, Ferrum, Va. Cat #11-00450). In experiments where textiles were inoculated, the odor controlling strains and the odorigenic strains were first grown in Luria-Bertani (LB) medium (Difco™ Cat #241420) to ensure growth under optimal conditions. After observing optimal growth in the LB media, the odor controlling bacterial strains and the odorigenic strains were grown in a second minimal medium (i.e., Glutamate-SBL) to mimic conditions in a washing machine. The Glutamate-SBL medium contained the following nutrients ($I^{-1}$): 1.9 g SBL2004 (WFK Cat #10996), 2.0 g L-glutamic acid (monosodium salt), 0.5 g $KH_2PO_4$, 0.2 g NaCl and 0.2 g $MgSO_4.7H_2O$. The pH of MG medium was adjusted to 7.0 with 3 M NaOH prior to autoclaving.

Textiles Pre-Washing:

Standard textiles from the Cleaning Technology Institute in Germany (WFK) cotton 10A (Order code 10000) and polyester 30A (Order code 30000) were cut in swatches of 2.54 cm×2.54 cm. The swatches were pre-washed five times prior to the experiments using a commercial detergent solution according to the label instructions.

Textiles Washing:

The washing process was carried out in 50 ml baffled flasks using 3.2 g of clean swatches (0.2 g textile/ml detergent solution) with 16 ml of detergent solution and 0.03 g SBL2004 soil ballasts (WFK) and covered with aluminum foil. Flasks were incubated at 30° C. with shaking (250 rpm) for 30 minutes on an orbital laboratory shaker (New Brunswick Innova 2300 Shaker). The washing solution was removed and the swatches were squeezed by hand to eliminate excess solution. A rinse was performed with 16 ml of deionized water shaking for 10 minutes, this was repeated twice. After the final rinse, the swatches were squeezed by hand, and under sterile conditions, to remove the excess of water and placed on clean pads (PIG High-visibility Mat-Pads Cat # MATT605, New PIG) for drying at room temperature.

Bacterial Inocula Preparation:

Gram positive odor controlling Bacillus strains (NRRL B-50141, PTA-7543, PTA-7549) and the following Gram negative odorigenic bacteria isolated from soiled clothes (Cronobacter sakazakii; Pseudomonas veronii; Pseudomonas marginalis, and Microbacterium luteolum) were cultivated on SMA medium at 30° C. overnight. A single colony from each of the odor controlling Bacillus strains (NRRL B-50141, PTA-7543, PTA-7549) and the odorigenic strains (*Cronobacter sakazakii; Pseudomonas veronii; Pseudomonas marginalis,* and *Microbacterium luteolum*) were inoculated in sterile tubes containing 4 ml LB broth, and incubated at 30° C. for 15 hours at 250 rpm. After incubation, the odor controlling *Bacillus* strains (NRRL B-50141, PTA-7543, PTA-7549) and the odorigenic strains (*Cronobacter sakazakii; Pseudomonas veronii; Pseudomonas marginalis,* and *Microbacterium luteolum*) were diluted 1:100 (equivalent to $10^3$ CFU per ml).

Following dilution, the odorigenic strains (*Cronobacter sakazakii; Pseudomonas veronii; Pseudomonas marginalis,* and *Microbacterium luteolum*) were combined to prepare an odorigenic bacterial mix. The odorigenic bacterial mix was prepared by mixing equal volumes of bacterial suspension from each of these odorigenic strains into a sterile tube.

The odor controlling *Bacillus* suspensions (i.e., NRRL B-50141, PTA-7543, PTA-7549) and the odorigenic bacterial mixture of strains (*Cronobacter sakazakii; Pseudomonas veronii; Pseudomonas marginalis,* and *Microbacterium luteolum*) were used to inoculate the textiles.

Textile Inoculation:

Two sets of flasks (Set-1 and Set-2 respectively) were prepared. Set-1 was used to count the bacterial populations and Set-2 was used for odor evaluation. Each set of flasks included three experimental flasks, one negative control flask, and one positive control flask (all 50 ml baffled flasks) for a total of five flasks per set.

3.2 g of prewashed swatches (cotton and polyester) were weighed and placed into each of the 50 ml baffled flasks with 16 ml of LB, covered with aluminum foil, and autoclaved at 121° C. for 30 minutes. The flasks and textiles were cooled inside of the laminar hood to room temperature. After cooling, each of the three experimental flasks and the positive control flask for Sets 1 and 2 respectively were inoculated.

Each of the three experimental flasks contained 3.2 g of prewashed swatches (cotton and polyester), and 160 μl of the odorigenic bacterial mixture (*Cronobacter sakazakii; Pseudomonas veronii; Pseudomonas marginalis,* and *Microbacterium luteolum*). Each of those three experimental flasks was further inoculated with 160 μl of a single odor controlling *Bacillus* suspension (i.e., NRRL B-50141, PTA-7543, and PTA-7549 respectively).

The positive control flask contained only 3.2 g of the prewashed swatches (cotton and polyester), and 160 μl of the odorigenic bacterial mixture (*Cronobacter sakazakii; Pseudomonas veronii; Pseudomonas marginalis,* and *Microbacterium luteolum*).

The negative control flask was not inoculated and contained only 3.2 g of prewashed swatches (cotton and polyester) and 16 ml of LB media.

The experimental procedure used above for textile inoculation was repeated. The only change in procedure was a substitution in the choice of media. Specifically, LB media was substituted with Glutamate-SBL media to mimic the environmental conditions of a washing machine.

Malodor Generation and Bacterial Populations.

Each set of experimental and control flasks as described above were incubated at 30° C. overnight at 87 rpm. The media was removed under sterile conditions and rinsed with sterile water for one minute.

In order to compare the populations of odor controlling *Bacillus* and odorigenic bacteria before washing, after washing, and 7-days post washing, the following procedure was performed using the flasks from Set-1 above. Bacterial populations (i.e., odor controlling *Bacillus* strains (NRRL B-50141, PTA-7543, PTA-7549) and the odorigenic strains (*Cronobacter sakazakii; Pseudomonas veronii; Pseudomonas marginalis,* and *Microbacterium luteolum*)) were compared and counted using the swatches from Set-1. Specifically, the swatches from the flask were transferred to 50 ml Falcon centrifuge tubes. The tubes were filled with 35 ml of phosphate buffer (Weber Scientific Cat #3127-29) and placed in a tumble shaker for 30 minutes. The swatches were removed and the tubes were centrifuged at 5,000 RPM for 10 minutes. The supernatant was discarded and the pellet was resuspended in 1 ml of phosphate buffer. Ten fold serial dilutions were made and plated on SMA and MacConkey media (selected for Gram negative bacterial populations). Plates were incubated at 30° C. overnight and CFUs were counted and reported in CFU per $cm^2$ of textile. To determine the population of odor controlling *Bacillus*, the number of CFU present on the MacConkey media (selective only for the Gram negative odorigenic bacteria (i.e., *Cronobacter sakazakii; Pseudomonas veronii; Pseudomonas marginalis,* and *Microbacterium luteolum*)) was subtracted from the total CFU from the non-selective SMA media.

To observe populations of odor controlling *Bacillus* (NRRL B-50141, PTA-7543, PTA-7549) and odorigenic bacteria (*Cronobacter sakazakii; Pseudomonas veronii; Pseudomonas marginalis,* and *Microbacterium luteolum*) after washing and after 7-days post-washing, the remnant swatches were washed as previously described (see above: Procedure "Textiles Pre-Washing" and "Textiles Washing") and the population of odor control *Bacillus* was determined immediately after washing according to the counting method previously discussed. The washed swatches were counted again after 7-days. Results provided in Tables 5 and 6 below (results measured by "log control").

Set 2 was washed as described by the protocol above (see above: Procedures "Textiles Pre-Washing" and "Textiles Washing"). After washing, textiles were transferred to a clean sterile 250-ml Erlenmeyer flask and sealed with aluminum foil aseptically for evaluation for odor by a sensory panel of volunteers.

TABLE 5

Bacterial populations on laundered textiles inoculated with different strains utilizing LB medium and washed with a commercial detergent.

| STRAIN | PRE-WASHED | AFTER WASHING (T = 0 DAYS) | AFTER WASHING (TIME = 7 DAYS) |
|---|---|---|---|
| ODORIGENIC MIX (OM) + NRRL B-50141 | OM = $6.3 \times 10^8$ NRRL B-50141 = $4.0 \times 10^8$ | OM = $5.7 \times 10^5$ NRRL B-50141 = $8.4 \times 10^5$ | OM = $6.9 \times 10^6$ NRRL B-50141 = $5.6 \times 10^6$ |
| ODORIGENIC MIX (OM) + PTA-7543 | OM = $3.4 \times 10^8$ PTA-7543 = $3.5 \times 10^7$ | OM = $6.3 \times 10^5$ PTA-7543 = $4.0 \times 10^5$ | OM = $8.3 \times 10^6$ PTA-7543 = $4.0 \times 10^6$ |

TABLE 5-continued

Bacterial populations on laundered textiles inoculated with different strains utilizing LB medium and washed with a commercial detergent.

| STRAIN | PRE-WASHED | AFTER WASHING (T = 0 DAYS) | AFTER WASHING (TIME = 7 DAYS) |
|---|---|---|---|
| ODORIGENIC MIX (OM) + PTA-7549 | OM = $3.4 \times 10^8$ PTA-7549 = $5.5 \times 10^8$ | OM = $3.4 \times 10^5$ PTA-7549 = $3.5 \times 10^5$ | OM = $3.4 \times 10^6$ PTA-7549 = $5.5 \times 10^6$ |

As reflected in Table 5, the total number of odor controlling *Bacillus* (NRRL B-50141, PTA-7543, PTA-7549) and odorigenic bacteria (*Cronobacter sakazakii*; *Pseudomonas veronii*; *Pseudomonas marginalis*, and *Microbacterium luteolum*) were reduced immediately after washing. Populations of odorigenic bacteria and odor controlling bacteria increased at 7-days.

TABLE 6

Bacterial populations on laundered textiles inoculated with different strains utilizing Glutamate-SBL medium and washed with a commercial detergent.

| STRAIN | PRE-WASHED | AFTER WASHING (T = 0 DAYS) | AFTER WASHING (TIME = 7 DAYS) |
|---|---|---|---|
| ODORIGENIC MIX (OM) + NRRL B-50141 | OM = $7.0 \times 10^6$ NRRL B-50141 = $6.7 \times 10^6$ | OM = $4.2 \times 10^4$ NRRL B-50141 = $8.4 \times 10^4$ | OM = $6.9 \times 10^6$ NRRL B-50141 = $4.6 \times 10^6$ |
| ODORIGENIC MIX (OM) + PTA-7543 | OM = $6.5 \times 10^6$ PTA-7543 = $5.5 \times 10^6$ | OM = $3.3 \times 10^4$ PTA-7543 = $4.0 \times 10^4$ | OM = $6.3 \times 10^6$ PTA-7543 = $4.0 \times 10^6$ |
| ODORIGENIC MIX (OM) + PTA-7549 | OM = $6.0 \times 10^6$ PTA-7549 = $5.5 \times 10^6$ | OM = $6.4 \times 10^4$ PTA-7549 = $3.5 \times 10^4$ | OM = $5.4 \times 10^6$ PTA-7549 = $3.5 \times 10^6$ |

As reflected in Table 6, the total number of odor controlling *Bacillus* (NRRL B-50141, PTA-7543, PTA-7549) and odorigenic mixture of bacteria (*Cronobacter sakazakii*; *Pseudomonas veronii*; *Pseudomonas marginalis*, and *Microbacterium luteolum*) were reduced immediately after washing. Populations of odorigenic bacteria and odor controlling bacteria increased at 7-days.

Sensory evaluation of washed swatches: Flasks from Set-2 were evaluated for odor by a sensory panel of volunteers at times 0, 24, 48 and 72 hours after washing as described above. The headspace over the wet samples was evaluated by a sensory panel (9-11 panelists). The odor intensity was evaluated by the following ranking: 0=No Detectable Odor; 1=Odor Almost Undetectable; 2=Odor Difficult to Detect; 3=Odor Easily Detectable; 4=Strong Offensive Odor 5=Sickening Odor. The samples were presented to the panelist in random order and evaluations were performed one minute between each sample. The time between each panelist was 20 minutes. Results provided in Table 7 below show the average scores for odor as determined by the odor panel.

TABLE 7

Average Odor Panel Results for Odorigenic Strains Mix (OM) Alone and in Combination with Odor Controlling *Bacillus* Strains

| TIME POST-WASHING (HOURS) | NEGATIVE CONTROL | POSITIVE CONTROL | OM + NNRL-50141 | OM + PTA-7543 | OM + PTA-7549 |
|---|---|---|---|---|---|
| 24 | 0.0 | 1.5 | 0.0 | 0.6 | 0.8 |
| 48 | 0.0 | 3.5 | 0.8 | 0.3 | 0.0 |
| 72 | 0.0 | 3.5 | 1.7 | 0.9 | 0.9 |

(OM) and co-cultivated with odor control (NRRL B-50141; PTA-7543; PTA-7549).
Where: 0 = No Detectable Odor; 1 = Odor Almost Undetectable; 2 = Odor Difficult to Detect; 3 = Odor Easily Detectable; 4 = Strong Offensive Odor As reflected in Table 7, the average scores, were the average scores compiled from an odor panel of volunteers, indicated that the odor of the positive control, containing the odorigenic mixture of strains (*Cronobacter sakazakii*; *Pseudomonas veronii*; *Pseudomonas marginalis*, and *Microbacterium luteolum*) only, was mitigated by the odor controlling *Bacillus* (NRRL B-50141, PTA-7543, PTA-7549) at 24, 48, and 72 hours respectively.

Example 6—Reduced Wash Machine Isolate Biofilm Formation and Planktonic Proliferation in Presence of *Bacillus* Candidates—Test Tube+Coupon Biocontrol (TTCBC)

The following example was conducted to determine whether certain odor controlling *Bacillus* strains (PTA-7543 and NRRL B-50706) are capable of inhibiting, and/or reducing the formation of biofilms by odorigenic wash machine isolates (ML5-1 [*Agrobacterium tumifaciens*], EL1-2 [*Micrococcus luteus*] and EL4-3 [*Rhodococcus opacus*]).

A polycarbonate holder (Biosurfaces Technology) with three stainless steel coupons (Biosurfaces Technology) and 50 ml of Luria-Bertani (LB) medium, (Difco DF241420) made according to label instructions, was added to nine individual wide-mouth test tubes (VWR cat #100483-220) and autoclaved. Of the nine test tubes, six were experimental test tubes and three were control test tubes. The first control test tube contained 400 μl of a 1:20 dilution of odorigenic wash machine isolate ML5-1. The second control test tube contained 400 μl of a 1:100 dilution of odorigenic wash machine isolate EL1-2. The third control test tube contained 400 μl of odorigenic wash machine isolate EL4-3. Dilutions of ML5-1, EL1-2, and EL4-3 were made based on growth kinetics and similar bacterial counts per tube.

The six experimental test tubes were inoculated with an overnight vegetative cell culture of an individual odor controlling *Bacillus* candidate and an overnight culture of an individual odorigenic wash machine isolate (PTA-7543 and ML5-1; PTA-7543 and EL1-2; PTA-7543 and EL4-3; NRRL B-50706 and ML5-1; NRRL B-50706 and EL1-2; NRRL B-50706 and EL4-3 respectively). Odor controlling *Bacillus* candidates (PTA-7543 and NRRL B-50706 were grown in LB for 18 to 24 hours resulting in $10^8$ CFU/ml culture and odorigenic wash machine isolates (ML5-1 [*Agrobacterium tumefaciens*], EL1-2 [*Micrococcus luteus*] and EL4-3 [*Rhodococcus opacus*]) were grown in LB for 18 to 24 hours (appx $10^6$ to $10^8$ culture). The nine test tubes were prepared in duplicate for sampling at 24 and 48 hours respectively.

The tubes were incubated at 30° C. with mild shaking. The initial dose of odor controlling *Bacillus* cells (PTA-7543 and NRRL B-50706) was in the range of $3 \times 10^3$ to $7 \times 10^3$ CFU/ml and the initial dose of odorigenic wash machine isolates (ML5-1 [*Agrobacterium tumifaciens*], EL1-2 [*Micrococcus luteus*] and EL4-3 [*Rhodococcus opacus*]) was in the range of $3 \times 10^3$ to $4 \times 10^3$ CFU/ml. The odorigenic wash machine isolate to odor controlling *Bacillus* ratios ranged from 1:1.65 to 1:2.18.

At time points 24 and 48 hours into incubation, the tubes were destructively sampled by scraping each coupon (biofilm cells) into phosphate buffered saline, homogenizing the suspension, then diluting and plating on MacConkey agar (Difco DF0075-17-1) to enumerate only ML5-1 or Tryptic Soy Agar (Difco DF236950)+30 μg/L Nalidixic Acid (Sigma-Aldrich cat # N4382-5G) to enumerate only EL1-2 and EL4-3. The broth in the tubes (planktonic cells) was also sampled, diluted and plated. Odorigenic wash machine isolate counts in the presence of odor controlling *Bacillus* spp. were compared to negative controls with no odor controlling *Bacillus* spp. present and the log control of odorigenic wash machine isolate for each odor controlling *Bacillus* candidate was calculated at times 24 and 48 hours for planktonic and attached cells. Results provided in Table 8 below.

TABLE 8

Log Control of Odorigenic Isolates

| STRAIN | WASH MACHINE ISOLATE:*BACILLUS* RATIO | | | LOG CONTROL* 24 HR PLANKTONIC | | | LOG CONTROL 24 HR ATTACHED | | | LOG CONTROL 48 HR PLANKTONIC | | | LOG CONTROL 48 HR ATTACHED | | |
|---|---|---|---|---|---|---|---|---|---|---|---|---|---|---|---|
| | ML5-1:XB | EL1-2:XB | EL4-3:XB | ML5-1 | EL1-2 | EL4-3 | ML5-1 | EL1-2 | EL4-3 | ML5-1 | EL1-2 | EL4-3 | ML5-1 | EL1-2 | EL4-3 |
| PTA-7543 | 2.18 | 1.65 | 1.72 | 4.94 | 4.76 | 4.18 | 4.32 | 4.12 | 3.83 | 4.04 | 5.73 | 3.74 | 3.66 | 4.68 | 2.8 |
| NRRL B-50706 | 1.13 | 1.49 | 1.43 | 3.40 | 3.23 | 3.03 | 4.00 | 2.89 | 3.07 | 4.37 | 4.1 | 1.19 | 3.54 | 4.23 | 1.46 |

*LOG CONTROL = LOG(WASH MACHINE ISOLATE ONLY) − LOG(WASH MACHINE ISOLATE IN PRESENCE OF *BACILLUS* STRAIN)

As reflected in Table 8, the growth of the odorigenic bacteria (ML5-1 [*Agrobacterium tumifaciens*], EL1-2 [*Micrococcus luteus*] and EL4-3 [*Rhodococcus opacus*]) was inhibited at 24 hours and 48 hours in the presence of odor controlling *Bacillus* cells (PTA-7543 and NRRL B-50706).

Example 7: Reduced Wash Machine Isolate Odor Production in Presence of *Bacillus* Isolates—Test Tube+Stainless Steel Washing Machine Component Coupon Luria-Bertani (LB) Medium The following example was conducted to determine whether certain odor controlling *Bacillus* strains (PTA-7543 and NRRL B-50706) are capable of inhibiting, preventing, and/or reducing the malodor cause in washing machines by odorigenic bacteria (ML5-1 [*Agrobacterium tumifaciens*], EL1-2 [*Micrococcus luteus*] and EL4-3 [*Rhodococcus opacus*]).

A polycarbonate holder (Biosurfaces Technology) with three stainless steel coupons (Biosurfaces Technology) and 50 ml of Luria-Bertani (LB) medium, (Difco DF241420) made according to label instructions, was added to nine individual wide-mouth test tubes (VWR cat #100483-220) and autoclaved. Of the nine test tubes, six were experimental test tubes and three were control test tubes. The first control test tube contained 400 μl of a 1:20 dilution of odorigenic wash machine isolate ML5-1. The second control test tube contained 400 μl of a 1:100 dilution of odorigenic wash machine isolate EL1-2. The third control test tube contained 400 μl of odorigenic wash machine isolate EL4-3. Dilutions of ML5-1, EL1-2, and EL4-3 were made based on growth kinetics and similar bacterial counts per tube.

The six experimental test tubes were inoculated with an overnight vegetative cell culture of an individual odor controlling *Bacillus* candidate and an overnight culture of an individual odorigenic wash machine isolate (PTA-7543 and ML5-1; PTA-7543 and EL1-2; PTA-7543 and EL4-3; NRRL B-50706 and ML5-1; NRRL B-50706 and EL1-2; NRRL B-50706 and EL4-3 respectively). Odor controlling *Bacillus* candidates (PTA-7543 and NRRL B-50706) were grown in LB for 18 to 24 hours resulting in $10^8$ CFU/ml culture and odorigenic wash machine isolates (ML5-1 [*Agrobacterium tumefaciens*], EL1-2 [*Micrococcus luteus*] and EL4-3 [*Rhodococcus opacus*]) were grown in LB for 18 to 24 hours (appx $10^6$ to $10^8$ culture). The nine test tubes were prepared in duplicate for sampling at 24 and 48 hours respectively.

The tubes were incubated at 30° C. with mild shaking. Initial dose of odor controlling *Bacillus* cells was in the range of $3\times10^3$ to $7\times10^3$ CFU/ml and initial dose of odorigenic wash machine isolate was in the range of $3\times10^3$ to $4\times10^3$ CFU/ml. The odorigenic wash machine isolate to odor controlling *Bacillus* ratios ranged from 1:1.65 to 1:2.18. At time points 24 and 48 hours into incubation, the tubes were destructively sampled by removing the coupons into a glass jar (Fisher cat #02-911-773). The malodor on the coupons in the glass jar acclimated overnight (approximately 17 hours). The jars were vented one hour before the odor panel started and then immediately recapped. The odor panel consisted of 5 volunteers. Volunteers opened each jar one at a time, smelled the contents, and rated the smell on a scale of 0 to 5; 0 being no odor, 1=slight odor, 2=weak odor, 3=moderate odor, 4=strong odor, and 5=offensive/extremely strong odor. There was a minute wait between asking volunteers to rate the smell of each jar. After one volunteer finished scoring the odors in each jar, there was an hour wait before the next volunteer sampled the jars. Results provided in Tables 9-11 below show the average scores for odor as determined by the odor panel.

TABLE 9

Average Odor Panel Results for Odorigenic Wash Machine Isolate ML5-1

| | Average Odor Intensity* | |
|---|---|---|
| | 24 Hour | 48 Hour |
| ML5-1 | 4.2 | 4.6 |
| PTA-7543 | 4 | 3.2 |
| ML5-1 + PTA-7543 | 2.8 | 3.8 |
| ML5-1 + NRRL B-50706 | 2.8 | 2.2 |
| NRRL B-50706 | 1.2 | 1.2 |

*Odor Intensity: 0 = no odor, 1 = slight odor, 2 = weak odor, 3 = moderate odor, 4 = strong odor, and 5 = offensive odor

TABLE 10

Average Odor Panel Results for Odorigenic Wash Machine Isolate EL1-2

| | Average Odor Intensity* | |
|---|---|---|
| | 24 Hour | 48 Hour |
| EL1-2 | 4 | 4.8 |
| EL1-2 + PTA-7543 | 3.6 | 2.2 |
| EL1-2 + NRRL B-50706 | 3.2 | 2 |
| PTA-7543 | 2.2 | 3.4 |
| NRRL B-50706 | 2 | 2.6 |

*Odor Intensity: 0 = no odor, 1 = slight odor, 2 = weak odor, 3 = moderate odor, 4 = strong odor, and 5 = offensive odor

TABLE 11

Average Odor Panel Results for Odorigenic Wash Machine Isolate EL4-3

| | Average Odor Intensity* | |
|---|---|---|
| | 24 Hour | 48 Hour |
| EL4-3 + NRRL B-50706 | 3.4 | 2 |
| NRRL B-50706 | 3.4 | 3.8 |
| EL4-3 + PTA-7543 | 3.2 | 3 |
| PTA-7543 | 3 | 2.4 |
| EL4-3 | 2 | 3.8 |

*Odor Intensity: 0 = no odor, 1 = slight odor, 2 = weak odor, 3 = moderate odor, 4 = strong odor, and 5 = offensive odor As reflected in Tables 9-11, the average scores, were the average scores compiled from an odor panel of volunteers, indicated that the odor of single odorigenic wash machine isolates (ML5-1 [*Agrobacterium tumefaciens*], EL1-2 [*Micrococcus luteus*] and EL4-3 [*Rhodococcus opacus*] respectively), in the presence of odor controlling *Bacillus* candidates (PTA-7543 and NRRL B-50706) were mitigated. PTA-7543 and NRRL B-50706 reduced the odor of ML5-1 at 24 and 48 hours, PTA-7543 and NRRL B-50706 reduced the odor of EL1-2 at 24 and 48 hours, and PTA-7543 and NRRL B-50706 reduced the odor of EL1-2 at 48 hours only.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. Various references are cited herein, the disclosures of which are incorporated by reference in their entireties.

We claim:

1. A method of inhibiting or reducing production of laundry malodor caused by at least one malodor causing bacteria comprising contacting a fabric or a laundry washing machine with a *Bacillus* strain having the deposit accession number NRRL B-50017, which inhibits or reduces production of malodor caused by the at least one malodor causing bacteria.

2. The method of claim 1, wherein the method comprises contacting the at least one malodor causing bacteria with the *Bacillus* strain.

3. The method of claim 1, wherein the method comprises contacting an odor generating compound derived from the at least one malodor causing bacteria with the *Bacillus* strain.

4. The method of claim 1, wherein the contacting comprises administering the *Bacillus* strain to a laundry washing machine.

5. The method of claim 1, wherein the contacting is done during a washing process.

6. The method of claim 1, wherein the contacting is done to a new washing machine.

7. The method of claim 1, wherein the contacting is done to a washing machine following one or more uses of said washing machine.

8. The method of claim 1, wherein the at least one malodor causing bacteria is at least one bacterial species selected from the group consisting of *Bacillus amyloliquefaciens, Acinetobacter junii, Bacillus subtilis, Janibacter*

*melois, Sphingobium ummariense, Sphingomonas panni, Sphingomonadaceae sp., Actinobacter tandoll, Junibacter melonis, Curtobacterium flaccumfaciens, Flavobacterium denitrificans, Staphylococcus epidermidis, Escherichia coli, Leclercia adecarboxylata, Enterobacter sp., Cronobacter sakazakii, Bacillus megaterium, Sphingobacterium faecium, Enterobacter cloacae, Pseudomonas veronfi, Microbacterium luteolum, Morganella morganii, Bacillus cereus, Pseudomonas sp., Pseudomonas-marginalis, Citrobacter sp., Escherichia coli* strain *JCLys*5, *Roseomonas aquatic, Pseudomonas panipatensis, Brevibacillus subtilis subtilis, Micrococcus luteus, Bacillus pumilus, Ralstonia eutropha, Caulobacter fusiformis, Stenotrophomonas maltophilia, Rhodococcus opacus, Breviundimonas intermedia, Agrobacterium tumefaciens,* and combinations thereof.

9. A method of inhibiting the production of laundry malodor caused by a bacterium, comprising contacting a laundry washing machine with a *Bacillus* strain, in combination with or formulated as a washing product, which inhibits the production of malodor caused by the at least one bacterium that causes laundry malodor;
   wherein the *Bacillus* strain is a strain having the deposit accession number NRRL B-50017,
   wherein the bacterium is selected from the group consisting of *Bacillus subtilis, Sphingobium ummariense, Sphingomonas panni, Sphingomonas ursinicola, Acinetobacter tandoii, Acinetobacter junfi, Curtobacterium flaccumfaciens, Janibacter melonis, Pseudomonas sp., Flavobacterium denitrificans, Micrococcus luteus, Bacillus pumilus, Ralstonia eutropha, Caulobacter fusiformis, Stenotrophomonas maltophilia, Micrococcus luteus, Rhodococcus opacus, Breviundimonas intermedia, Agrobacterium tumefaciens* and a combination thereof.

10. The method of claim 9, wherein the method comprises contacting the at least one bacterium that causes laundry malodor.

11. The method of claim 9, wherein the method comprises contacting an odor generating compound obtained from the at least one bacterium capable of causing odor.

12. The method of claim 9, wherein the contacting is done during a washing process.

13. The method of claim 9, wherein the contacting is done to a new washing machine.

14. The method of claim 9, wherein the contacting is done to a washing machine following one or more uses of said washing machine.

* * * * *